(12) United States Patent
Marambaud et al.

(10) Patent No.: US 8,420,309 B2
(45) Date of Patent: Apr. 16, 2013

(54) METHOD OF SCREENING COMPOUNDS USING CALHM (FAM26C)

(75) Inventors: Philippe Marambaud, Astoria, NY (US); Fabien Campagne, Astoria, NY (US)

(73) Assignees: The Feinstein for Medical Research, Manhasset, NY (US); Cornell Research Foundation, Inc., Ithaca, NY (US)

( * ) Notice: Subject to any disclaimer, the term of this patent is extended or adjusted under 35 U.S.C. 154(b) by 149 days.

(21) Appl. No.: 12/733,096

(22) PCT Filed: Aug. 8, 2008

(86) PCT No.: PCT/US2008/009556
§ 371 (c)(1),
(2), (4) Date: Feb. 8, 2011

(87) PCT Pub. No.: WO2009/023145
PCT Pub. Date: Feb. 19, 2009

(65) Prior Publication Data
US 2011/0123984 A1   May 26, 2011

Related U.S. Application Data

(60) Provisional application No. 60/964,282, filed on Aug. 10, 2007.

(51) Int. Cl.
| | |
|---|---|
| *A61P 25/28* | (2006.01) |
| *C40B 30/00* | (2006.01) |
| *C40B 30/06* | (2006.01) |
| *C12Q 3/00* | (2006.01) |
| *C12Q 1/68* | (2006.01) |
| *A61K 38/00* | (2006.01) |
| *C07K 1/00* | (2006.01) |

(52) U.S. Cl.
USPC ....... 435/4; 435/6.1; 506/7; 514/1.1; 530/350
(58) Field of Classification Search .................. None
See application file for complete search history.

(56) References Cited

U.S. PATENT DOCUMENTS

2002/0086300 A1   7/2002   Adler et al.

OTHER PUBLICATIONS

GenBank hypothetical protein LOC255022 [*Homo sapiens*], Locus NP_001001412 (May 28, 2004), from www.ncbi.nlm.nih.gov, pp. 1-2.*

(Continued)

*Primary Examiner* — Jeffrey Stucker
*Assistant Examiner* — Adam M Weidner
(74) *Attorney, Agent, or Firm* — Amster, Rothstein & Ebenstein LLP

(57) ABSTRACT

Provided are methods of screening test compounds for the ability to alter calcium homeostasis in mammalian cells by experimentally determining if a compound affects CALHM1, CALHM2, or CALHM3 expression or activity. Additionally provided are methods of screening a test compound for the ability to inhibit ERK 1/2 phosphorylation in a mammalian cell. Further provided are methods of screening a test compound for the ability to inhibit amyloid-beta peptide accumulation in a mammalian cell or biological fluid, methods of screening for a test compound that may affect Alzheimer's disease and methods of determining the likelihood that a subject will be diagnosed with Alzheimer's disease. Also provided are isolated and purified mammalian CALHM proteins, vectors comprising a nucleic acid sequence encoding the CALHM1, CALHM2, and CALHM3 proteins, and mammalian cells transfected with the vectors. Additionally, methods of affecting Ca2+ levels in a mammalian cell are provided.

36 Claims, 5 Drawing Sheets

OTHER PUBLICATIONS dbSNP details for ss39737339 (Jul. 16, 2005) from www.ncbi.nlm.nih.gov, p. 1.*
Bertram et al. 2000 "evidence for genetic linkage of Alzheimer's disease to chromosome 10q" Science 290:2302.*
Bertram et al. 2006 "single-nucleotide polymorphism rs498055 on chromosome 10q24 is not associated with alzheimer disease in two independent family samples" American J Human Genetics 79:180-187.*
PCT International Search Report dated Feb. 27, 2009 in connection with PCT International Patent Application No. PCT/US2008/09556, 7 pages.
PCT Written Opinion of the International Searching Authority dated Feb. 27, 2009 in connection with PCT International Patent Application No. PCT/US2008/09556, 5 pages.
Gen Bank Accession No: NT_030059.12 (May 7, 2007). Retrieved from the internet Dec. 11, 2009: <http://www.ncbi.nlm.nih.gov/SNP/snp_ss.cpi?subsnp_id=71645063>, 2 pages.
Dreses-Werringloer U et al., entitled "A Polymorphism in CALHM1 Influences Ca2+ Homeostasis, Aβ Levels, and Alzheimer's Disease Risk," Cell 133, 1149-1161, Jun. 27, 2008.

* cited by examiner

SEQUENCE LISTING

```
<160> NUMBER OF SEQ ID NOS: 43

<210> SEQ ID NO 1
<211> LENGTH: 24
<212> TYPE: DNA
<213> ORGANISM: artificial
<220> FEATURE:
<223> OTHER INFORMATION: Beta-actin PCR primer

<400> SEQUENCE: 1
ctccttaatg tcacgcacga tttc                                          24

<210> SEQ ID NO 2
<211> LENGTH: 21
<212> TYPE: DNA
<213> ORGANISM: artificial
<220> FEATURE:
<223> OTHER INFORMATION: Beta-actin PCR primer

<400> SEQUENCE: 2
gccaaccgcg agaagatgac c                                             21

<210> SEQ ID NO 3
<211> LENGTH: 20
<212> TYPE: DNA
<213> ORGANISM: artificial
<220> FEATURE:
<223> OTHER INFORMATION: CALHM1 PCR primer

<400> SEQUENCE: 3
tgcttcctct gtgccttctg                                               20

<210> SEQ ID NO 4
<211> LENGTH: 20
```

```
<212> TYPE: DNA
<213> ORGANISM: artificial
<220> FEATURE:
<223> OTHER INFORMATION: CALHM1 PCR primer

<400> SEQUENCE: 4
ctccaggtca tggttcatgg                                              20

<210> SEQ ID NO 5
<211> LENGTH: 20
<212> TYPE: DNA
<213> ORGANISM: artificial
<220> FEATURE:
<223> OTHER INFORMATION: CALHM1 exon 1 PCR primer FX1US

<400> SEQUENCE: 5
tcttggaggc agcagtgagt                                              20

<210> SEQ ID NO 6
<211> LENGTH: 22
<212> TYPE: DNA
<213> ORGANISM: artificial
<220> FEATURE:
<223> OTHER INFORMATION: CALHM1 exon 1 PCR primer FX1DSa

<400> SEQUENCE: 6
ttttgagagg taggggata gg                                            22

<210> SEQ ID NO 7
<211> LENGTH: 20
<212> TYPE: DNA
<213> ORGANISM: artificial
<220> FEATURE:
<223> OTHER INFORMATION: CALHM1 exon 2 PCR primer FX2US

<400> SEQUENCE: 7
gctttgggag tctgaacagg                                              20

<210> SEQ ID NO 8
<211> LENGTH: 20
<212> TYPE: DNA
<213> ORGANISM: artificial
<220> FEATURE:
<223> OTHER INFORMATION: CALHM1 exon 2 PCR primer FX2DS

<400> SEQUENCE: 8
tcctttttcc acctggtttg                                              20

<210> SEQ ID NO 9
<211> LENGTH: 19
<212> TYPE: DNA
<213> ORGANISM: artificial
<220> FEATURE:
<223> OTHER INFORMATION: PCR primer for P86L genotyping

<400> SEQUENCE: 9
gaagagtgga agcggccac                                               19

<210> SEQ ID NO 10
<211> LENGTH: 19
<212> TYPE: DNA
<213> ORGANISM: artificial
<220> FEATURE:
<223> OTHER INFORMATION: PCR primer for P86L genotyping

<400> SEQUENCE: 10
gacggccacc cagacgaca                                               19
```

```
<210> SEQ ID NO 11
<211> LENGTH: 19
<212> TYPE: DNA
<213> ORGANISM: artificial
<220> FEATURE:
<223> OTHER INFORMATION: PCR primer for P86L genotyping

<400> SEQUENCE: 11
gaagagtgga agcggcagc                                                19

<210> SEQ ID NO 12
<211> LENGTH: 19
<212> TYPE: DNA
<213> ORGANISM: artificial
<220> FEATURE:
<223> OTHER INFORMATION: PCR primer for P86L genotyping

<400> SEQUENCE: 12
gaggaagcat ttgccgtcg                                                19

<210> SEQ ID NO 13
<211> LENGTH: 20
<212> TYPE: DNA
<213> ORGANISM: artificial
<220> FEATURE:
<223> OTHER INFORMATION: PCR primer for P86L genotyping

<400> SEQUENCE: 13
cctggtgctc tttctgcttg                                               20

<210> SEQ ID NO 14
<211> LENGTH: 18
<212> TYPE: DNA
<213> ORGANISM: artificial
<220> FEATURE:
<223> OTHER INFORMATION: PCR primer for P86L genotyping

<400> SEQUENCE: 14
cagaaggcag aggaagca                                                 18

<210> SEQ ID NO 15
<211> LENGTH: 350
<212> TYPE: PRT
<213> ORGANISM: Homo sapiens

<400> SEQUENCE: 15
```

Met Asp Lys Phe Arg Met Leu Phe Gln His Phe Gln Ser Ser Ser Glu
1               5                   10                  15

Ser Val Met Asn Gly Ile Cys Leu Leu Leu Ala Ala Val Thr Val Lys
            20                  25                  30

Leu Tyr Ser Ser Phe Asp Phe Asn Cys Pro Cys Leu Val His Tyr Asn
        35                  40                  45

Ala Leu Tyr Gly Leu Gly Leu Leu Leu Thr Pro Pro Leu Ala Leu Phe
    50                  55                  60

Leu Cys Gly Leu Leu Ala Asn Arg Gln Ser Val Val Met Val Glu Glu
65                  70                  75                  80

Trp Arg Arg Pro Ala Gly His Arg Arg Lys Asp Pro Gly Ile Ile Arg
                85                  90                  95

Tyr Met Cys Ser Ser Val Leu Gln Arg Ala Leu Ala Ala Pro Leu Val
            100                 105                 110

Trp Ile Leu Leu Ala Leu Leu Asp Gly Lys Cys Phe Val Cys Ala Phe
        115                 120                 125

Ser Ser Ser Val Asp Pro Glu Lys Phe Leu Asp Phe Ala Asn Met Thr
    130                 135                 140

Pro Ser Gln Val Gln Leu Phe Leu Ala Lys Val Pro Cys Lys Glu Asp
145                 150                 155                 160

Glu Leu Val Arg Asp Ser Pro Ala Arg Lys Ala Val Ser Arg Tyr Leu
                165                 170                 175

Arg Cys Leu Ser Gln Ala Ile Gly Trp Ser Val Thr Leu Leu Leu Ile
            180                 185                 190

Ile Ala Ala Phe Leu Ala Arg Cys Leu Arg Pro Cys Phe Asp Gln Thr
        195                 200                 205

Val Phe Leu Gln Arg Arg Tyr Trp Ser Asn Tyr Val Asp Leu Glu Gln
    210                 215                 220

Lys Leu Phe Asp Glu Thr Cys Cys Glu His Ala Arg Asp Phe Ala His
225                 230                 235                 240

Arg Cys Val Leu His Phe Phe Ala Ser Met Arg Ser Glu Leu Gln Ala
                245                 250                 255

Arg Gly Leu Arg Arg Gly Asn Ala Gly Arg Arg Leu Glu Leu Pro Ala
            260                 265                 270

Val Pro Glu Pro Pro Ala Val Pro Glu Pro Pro Glu Gly Leu Asp Ser
        275                 280                 285

Gly Ser Gly Lys Ala His Leu Arg Ala Ile Ser Ser Arg Glu Gln Val
    290                 295                 300

Asp Arg Leu Leu Ser Thr Trp Tyr Ser Ser Lys Pro Pro Leu Asp Leu
305                 310                 315                 320

Ala Ala Ser Pro Gly Leu Cys Gly Gly Leu Ser His Arg Ala Pro
                325                 330                 335

Thr Leu Ala Leu Gly Thr Arg Leu Ser Gln His Thr Asp Val
            340                 345                 350

<210> SEQ ID NO 16
<211> LENGTH: 323
<212> TYPE: PRT
<213> ORGANISM: Homo sapiens

<400> SEQUENCE: 16

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
            20                  25                  30

Val Gly Ser Gln Glu Leu Phe Ser Val Val Ala Phe His Cys Pro Cys
        35                  40                  45

Ser Pro Ala Arg Asn Tyr Leu Tyr Gly Leu Ala Ala Ile Gly Val Pro
    50                  55                  60

Ala Leu Val Leu Phe Ile Ile Gly Ile Ile Leu Asn Asn His Thr Trp
65                  70                  75                  80

Asn Leu Val Ala Glu Cys Gln His Arg Arg Thr Lys Asn Cys Ser Ala
                85                  90                  95

Ala Pro Thr Phe Leu Leu Leu Ser Ser Ile Leu Gly Arg Ala Ala Val
            100                 105                 110

Ala Pro Val Thr Trp Ser Val Ile Ser Leu Leu Arg Gly Glu Ala Tyr
        115                 120                 125

Val Cys Ala Leu Ser Glu Phe Val Asp Pro Ser Ser Leu Thr Ala Arg
    130                 135                 140

Glu Glu His Phe Pro Ser Ala His Ala Thr Glu Ile Leu Ala Arg Phe
145                 150                 155                 160

```
Pro Cys Lys Glu Asn Pro Asp Asn Leu Ser Asp Phe Arg Glu Val
            165                 170                 175

Ser Arg Arg Leu Arg Tyr Glu Ser Gln Leu Phe Gly Trp Leu Leu Ile
            180                 185                 190

Gly Val Val Ala Ile Leu Val Phe Leu Thr Lys Cys Leu Lys His Tyr
                195                 200                 205

Cys Ser Pro Leu Ser Tyr Arg Gln Glu Ala Tyr Trp Ala Gln Tyr Arg
210                 215                 220

Ala Asn Glu Asp Gln Leu Phe Gln Arg Thr Ala Glu Val His Ser Arg
225                 230                 235                 240

Val Leu Ala Ala Asn Asn Val Arg Arg Phe Phe Gly Phe Val Ala Leu
                245                 250                 255

Asn Lys Asp Asp Glu Glu Leu Ile Ala Asn Phe Pro Val Glu Gly Thr
                260                 265                 270

Gln Pro Arg Pro Gln Trp Asn Ala Ile Thr Gly Val Tyr Leu Tyr Arg
            275                 280                 285

Glu Asn Gln Gly Leu Pro Leu Tyr Ser Arg Leu His Lys Trp Ala Gln
290                 295                 300

Gly Leu Ala Gly Asn Gly Ala Ala Pro Asp Asn Val Glu Met Ala Leu
305                 310                 315                 320

Leu Pro Ser

<210> SEQ ID NO 17
<211> LENGTH: 346
<212> TYPE: PRT
<213> ORGANISM: Homo sapiens

<400> SEQUENCE: 17

Met Met Asp Lys Phe Arg Met Ile Phe Gln Phe Leu Gln Ser Asn Gln
1               5                   10                  15

Glu Ser Phe Met Asn Gly Ile Cys Gly Ile Met Ala Leu Ala Ser Ala
                20                  25                  30

Gln Met Tyr Ser Ala Phe Asp Phe Asn Cys Pro Cys Leu Pro Gly Tyr
            35                  40                  45

Asn Ala Ala Tyr Ser Ala Gly Ile Leu Leu Ala Pro Pro Leu Val Leu
        50                  55                  60

Phe Leu Leu Gly Leu Val Met Asn Asn Asn Val Ser Met Leu Ala Glu
65                  70                  75                  80

Glu Trp Lys Arg Pro Leu Gly Arg Arg Ala Lys Asp Pro Ala Val Leu
                85                  90                  95

Arg Tyr Met Phe Cys Ser Met Ala Gln Arg Ala Leu Ile Ala Pro Val
            100                 105                 110

Val Trp Val Ala Val Thr Leu Leu Asp Gly Lys Cys Phe Leu Cys Ala
        115                 120                 125

Phe Cys Thr Ala Val Pro Val Ser Ala Leu Gly Asn Gly Ser Leu Ala
            130                 135                 140

Pro Gly Leu Pro Ala Pro Glu Leu Ala Arg Leu Leu Ala Arg Val Pro
145                 150                 155                 160

Cys Pro Glu Ile Tyr Asp Gly Asp Trp Leu Leu Ala Arg Glu Val Ala
                165                 170                 175

Val Arg Tyr Leu Arg Cys Ile Ser Gln Ala Leu Gly Trp Ser Phe Val
            180                 185                 190

Leu Leu Thr Thr Leu Leu Ala Phe Val Val Arg Ser Val Arg Pro Cys
        195                 200                 205
```

```
Phe Thr Gln Ala Ala Phe Leu Lys Ser Lys Tyr Trp Ser His Tyr Ile
    210                 215                 220

Asp Ile Glu Arg Lys Leu Phe Asp Glu Thr Cys Thr Glu His Ala Lys
225                 230                 235                 240

Ala Phe Ala Lys Val Cys Ile Gln Gln Phe Glu Ala Met Asn His
                245                 250                 255

Asp Leu Glu Leu Gly His Thr His Gly Thr Leu Ala Thr Ala Pro Ala
                260                 265                 270

Ser Ala Ala Pro Thr Thr Pro Asp Gly Ala Glu Glu Arg Glu
    275                 280                 285

Lys Leu Arg Gly Ile Thr Asp Gln Gly Thr Met Asn Arg Leu Leu Thr
    290                 295                 300

Ser Trp His Lys Cys Lys Pro Pro Leu Arg Leu Gly Gln Glu Glu Pro
305                 310                 315                 320

Pro Leu Met Gly Asn Gly Trp Ala Gly Gly Pro Arg Pro Pro Arg
                325                 330                 335

Lys Glu Val Ala Thr Tyr Phe Ser Lys Val
                340                 345

<210> SEQ ID NO 18
<211> LENGTH: 348
<212> TYPE: PRT
<213> ORGANISM: mouse

<400> SEQUENCE: 18

Met Asp Lys Phe Arg Met Ile Phe Gln Phe Leu Gln Ser Asn Gln Glu
1               5                   10                  15

Ser Phe Met Asn Gly Ile Cys Gly Ile Met Ala Leu Ala Ser Ala Gln
                20                  25                  30

Met Tyr Ser Ala Phe Asp Phe Asn Cys Pro Cys Leu Pro Gly Tyr Asn
                35                  40                  45

Val Val Tyr Ser Leu Gly Ile Leu Leu Thr Pro Pro Leu Val Leu Phe
    50                  55                  60

Leu Leu Gly Leu Val Met Asn Asn Asn Ile Ser Met Leu Ala Glu Glu
65                  70                  75                  80

Trp Lys Arg Pro Ala Gly Arg Arg Ala Lys Asp Pro Ala Val Leu Arg
                85                  90                  95

Tyr Met Phe Cys Ser Met Ala Gln Arg Ala Leu Ile Ala Pro Val Val
                100                 105                 110

Trp Val Ala Val Thr Leu Leu Asp Gly Lys Cys Phe Leu Cys Ala Phe
            115                 120                 125

Cys Thr Ala Val Pro Val Ala Thr Leu Gly Asn Gly Ser Leu Val Pro
130                 135                 140

Gly Leu Pro Ala Pro Glu Leu Ala Arg Leu Leu Ala Arg Val Pro Cys
145                 150                 155                 160

Pro Glu Ile Tyr Asp Gly Asn Trp Leu Leu Ala Arg Glu Val Ala Val
                165                 170                 175

Arg Tyr Leu Arg Cys Ile Ser Gln Ala Leu Gly Trp Ser Phe Val Leu
                180                 185                 190

Leu Thr Thr Leu Leu Ala Phe Val Val Arg Ser Val Arg Pro Cys Phe
            195                 200                 205

Thr Gln Val Ala Phe Leu Lys Ser Lys Tyr Trp Ser His Tyr Ile Asp
    210                 215                 220

Ile Glu Arg Lys Leu Phe Asp Glu Thr Cys Thr Glu His Ala Lys Ala
225                 230                 235                 240
```

```
Phe Ala Lys Val Cys Ile Gln Gln Phe Phe Glu Ala Met Asn His Asp
                245                 250                 255

Leu Glu Leu Gly His Thr His Gly Val Leu Ala Thr Ala Thr Ala Thr
            260                 265                 270

Ala Thr Ala Thr Glu Ala Val Gln Ser Pro Ser Asp Arg Thr Glu Glu
            275                 280                 285

Glu Arg Glu Lys Leu Arg Gly Ile Thr Asp Gln Gly Thr Met Asn Arg
            290                 295                 300

Leu Leu Thr Ser Trp His Lys Cys Lys Pro Pro Leu Arg Leu Gly Gln
305                 310                 315                 320

Glu Ala Pro Leu Met Ser Asn Gly Trp Ala Gly Gly Glu Pro Arg Pro
                325                 330                 335

Pro Arg Lys Glu Val Ala Thr Tyr Phe Ser Lys Val
            340                 345

<210> SEQ ID NO 19
<211> LENGTH: 329
<212> TYPE: PRT
<213> ORGANISM: Caenorhabditis elegans

<400> SEQUENCE: 19

Met Thr Thr Ser Ile Asn Ser Val Val Thr Val Phe Gln Asn Val Phe
1               5                   10                  15

Thr Asn His Gly Ser Thr Leu Leu Asn Gly Ile Leu Ile Ala Thr Thr
            20                  25                  30

Val Gly Gly Gln Ser Leu Val Arg Lys Leu Thr Phe Ser Cys Pro Cys
        35                  40                  45

Ala Tyr Pro Leu Asn Ile Tyr His Ser Leu Val Phe Met Phe Gly Pro
    50                  55                  60

Thr Ala Ala Leu Leu Leu Ile Gly Ile Thr Val Asn Ser Thr Thr Trp
65                  70                  75                  80

Lys Leu Ala His Gly Phe Phe Phe Arg Val Arg Asp Thr Arg His Ser
                85                  90                  95

Trp Lys Thr Thr Cys Val Ser Trp Ile Glu Val Leu Ile Gln Ser Ser
            100                 105                 110

Val Ala Pro Ile Ala Trp Leu Phe Val Val Phe Leu Asp Gly Gly Tyr
        115                 120                 125

Tyr Arg Cys Tyr Arg Ser His Glu Phe Cys Leu Ile Ser Asp Ala Ile
    130                 135                 140

Leu Cys Lys Asn Ser Thr Ile Leu Asn Ser Tyr Ala Ser Thr Ser Ser
145                 150                 155                 160

Phe Asn Lys Ile Ser Asp Asn Gly Lys Tyr Cys Pro Pro Cys Ile Cys
                165                 170                 175

Val Pro Asn Pro Thr Asp Ala Ser Tyr Leu Glu Ala Glu Ser Gln Ile
            180                 185                 190

Tyr Ala Trp Gly Leu Leu Leu Phe Ser Gly Val Ala Ala Phe Leu Val
        195                 200                 205

Ile Thr Cys Asn Arg Met Cys Asp Lys Tyr Thr Leu Val Gln Arg Gln
    210                 215                 220

Tyr Val Glu Thr Tyr Lys Asn Val Glu Thr Gln Lys Phe Asp Ala Val
225                 230                 235                 240

Ala Lys Glu His Ala Ser Gln Leu Ala Glu His Asn Ala Arg Ala Phe
                245                 250                 255

Phe Gly Gln Lys Asp Trp Thr Lys Arg Asp Trp Asp Thr Val Ser Gly
            260                 265                 270
```

Ile Pro Glu Val Asn Asn Pro Leu Phe Ala Arg Leu Arg Leu Ile Ala
            275                 280                 285

Ala Glu Lys Thr Gln Gln Thr Met Tyr Thr Pro Leu Gln Leu Trp Asn
            290                 295                 300

Asp Asn Lys Gly Tyr Arg Ile Pro Gln Pro Asp Leu Gln Leu Thr Gln
305                 310                 315                 320

Ile Ile Val Asp Glu Thr Lys Glu Asp
                325

<210> SEQ ID NO 20
<211> LENGTH: 18
<212> TYPE: PRT
<213> ORGANISM: Homo sapiens

<400> SEQUENCE: 20

Ser Ile Trp Leu Leu Trp Ala Leu Val Phe Asn Asn Ser Val Pro Val
1               5                   10                  15

Glu Asn

<210> SEQ ID NO 21
<211> LENGTH: 18
<212> TYPE: PRT
<213> ORGANISM: Homo sapiens

<400> SEQUENCE: 21

Ser Val Trp Leu Leu Trp Ala Leu Val Phe Asn Asn Ser Val Pro Ile
1               5                   10                  15

Glu Asn

<210> SEQ ID NO 22
<211> LENGTH: 18
<212> TYPE: PRT
<213> ORGANISM: Homo sapiens

<400> SEQUENCE: 22

Ala Ile Trp Leu Leu Trp Gly Leu Val Phe Asn Asn Ser Val Pro Val
1               5                   10                  15

Gln Asn

<210> SEQ ID NO 23
<211> LENGTH: 18
<212> TYPE: PRT
<213> ORGANISM: Homo sapiens

<400> SEQUENCE: 23

Ala Ile Trp Leu Leu Trp Gly Leu Val Phe Asn Asn Ser Val Pro Val
1               5                   10                  15

Gln Asn

<210> SEQ ID NO 24
<211> LENGTH: 18
<212> TYPE: PRT
<213> ORGANISM: Homo sapiens

<400> SEQUENCE: 24

Leu Val Leu Phe Leu Leu Gly Leu Val Met Asn Asn Asn Val Ser Met
1               5                   10                  15

Leu Ala

<210> SEQ ID NO 25
<211> LENGTH: 18

```
<212> TYPE: PRT
<213> ORGANISM: chimpanzee

<400> SEQUENCE: 25

Leu Val Leu Phe Leu Leu Gly Leu Val Met Asn Asn Asn Val Ser Met
1               5                   10                  15

Leu Ala

<210> SEQ ID NO 26
<211> LENGTH: 18
<212> TYPE: PRT
<213> ORGANISM: macaque

<400> SEQUENCE: 26

Leu Val Leu Phe Leu Leu Gly Leu Val Met Asn Asn Asn Val Ser Met
1               5                   10                  15

Leu Ala

<210> SEQ ID NO 27
<211> LENGTH: 18
<212> TYPE: PRT
<213> ORGANISM: opossum

<400> SEQUENCE: 27

Leu Val Leu Phe Leu Leu Gly Leu Val Met Asn Asn Asn Val Ser Met
1               5                   10                  15

Leu Ala

<210> SEQ ID NO 28
<211> LENGTH: 18
<212> TYPE: PRT
<213> ORGANISM: elephant

<400> SEQUENCE: 28

Leu Val Leu Phe Leu Leu Gly Leu Val Met Asn Asn Asn Val Ser Met
1               5                   10                  15

Leu Ala

<210> SEQ ID NO 29
<211> LENGTH: 18
<212> TYPE: PRT
<213> ORGANISM: cat

<400> SEQUENCE: 29

Leu Val Leu Phe Leu Leu Gly Leu Val Met Asn Asn Asn Val Ser Met
1               5                   10                  15

Leu Ala

<210> SEQ ID NO 30
<211> LENGTH: 18
<212> TYPE: PRT
<213> ORGANISM: cow

<400> SEQUENCE: 30

Leu Val Leu Phe Leu Leu Gly Leu Val Met Asn Asn Asn Val Ser Met
1               5                   10                  15

Leu Ala

<210> SEQ ID NO 31
<211> LENGTH: 18
<212> TYPE: PRT
<213> ORGANISM: rat
```

<400> SEQUENCE: 31

Leu Val Leu Phe Leu Leu Gly Leu Val Met Asn Asn Asn Ile Ser Met
1               5                   10                  15

Leu Ala

<210> SEQ ID NO 32
<211> LENGTH: 18
<212> TYPE: PRT
<213> ORGANISM: mouse

<400> SEQUENCE: 32

Leu Val Leu Phe Leu Leu Gly Leu Val Met Asn Asn Asn Ile Ser Met
1               5                   10                  15

Leu Ala

<210> SEQ ID NO 33
<211> LENGTH: 18
<212> TYPE: PRT
<213> ORGANISM: dog

<400> SEQUENCE: 33

Leu Val Leu Phe Leu Leu Gly Leu Val Met Asn Asn Asn Val Ser Val
1               5                   10                  15

Leu Ala

<210> SEQ ID NO 34
<211> LENGTH: 18
<212> TYPE: PRT
<213> ORGANISM: platypus

<400> SEQUENCE: 34

Ala Val Leu Phe Leu Leu Gly Leu Val Met Asn Asn Asn Val Ser Met
1               5                   10                  15

Leu Ala

<210> SEQ ID NO 35
<211> LENGTH: 18
<212> TYPE: PRT
<213> ORGANISM: armadillo

<400> SEQUENCE: 35

Leu Leu Leu Phe Leu Leu Gly Leu Val Leu Asn Asn Asn Val Ser Met
1               5                   10                  15

Leu Ala

<210> SEQ ID NO 36
<211> LENGTH: 18
<212> TYPE: PRT
<213> ORGANISM: hedgehog

<400> SEQUENCE: 36

Leu Leu Leu Phe Leu Leu Gly Leu Val Leu Asn Asn Asn Val Ser Met
1               5                   10                  15

Leu Ala

<210> SEQ ID NO 37
<211> LENGTH: 18
<212> TYPE: PRT
<213> ORGANISM: chicken

<400> SEQUENCE: 37

```
Leu Ile Leu Phe Leu Leu Gly Phe Val Leu Asn Asn Asn Val Ser Met
1               5                   10                  15

Leu Ala

<210> SEQ ID NO 38
<211> LENGTH: 18
<212> TYPE: PRT
<213> ORGANISM: zebrafish

<400> SEQUENCE: 38

Ile Trp Phe Phe Leu Leu Gly Phe Val Leu Asn Asn Asn Val Ser Met
1               5                   10                  15

Leu Ala

<210> SEQ ID NO 39
<211> LENGTH: 18
<212> TYPE: PRT
<213> ORGANISM: medaka

<400> SEQUENCE: 39

Ile Trp Phe Phe Leu Leu Gly Phe Val Leu Asn Asn Asn Val Ser Val
1               5                   10                  15

Leu Ala

<210> SEQ ID NO 40
<211> LENGTH: 18
<212> TYPE: PRT
<213> ORGANISM: tetraodon

<400> SEQUENCE: 40

Ile Trp Phe Phe Met Leu Gly Phe Val Leu Asn Asn Asn Val Ser Val
1               5                   10                  15

Leu Ala

<210> SEQ ID NO 41
<211> LENGTH: 18
<212> TYPE: PRT
<213> ORGANISM: fugo

<400> SEQUENCE: 41

Ile Trp Phe Phe Met Leu Gly Phe Val Leu Asn Asn Asn Val Ser Val
1               5                   10                  15

Leu Ala

<210> SEQ ID NO 42
<211> LENGTH: 18
<212> TYPE: PRT
<213> ORGANISM: stickleback

<400> SEQUENCE: 42

Val Trp Phe Phe Leu Ile Gly Phe Val Leu Asn Asn Lys Val Ser Val
1               5                   10                  15

Leu Thr

<210> SEQ ID NO 43
<211> LENGTH: 801
<212> TYPE: DNA
<213> ORGANISM: Homo sapiens
<220> FEATURE:
<221> NAME/KEY: misc_feature
<222> LOCATION: (401)..(401)
<223> OTHER INFORMATION: n= a or g
```

```
<400> SEQUENCE: 43
acctgagcag aggccccatt ttgagaggta gggggatagg gccctcccag agggaccttg     60
atctgccagg gagacccagc gtgaagccat gcggcccctc acctgggaga tgcagcggag    120
gtaacgcacg gccacctctc gggccaacag ccagtcgcca tcgtagatct cagggcaggg    180
cacccgggcc agcaggcggg cgagctcggg ggcaggaagg ccgggtgcca ggctgccgtt    240
gcccagtgcg ctcacgggca cggcagtgca gaaggcacag aggaagcatt tgccgtcgag    300
tagcgtgacg gccacccaga cgacaggcgc gatgagggcg cgctgggcca tggagcagaa    360
catgtagcgc aacacagcgg ggtccttggc ccggcggccc ngcggccgct tccactcttc    420
ggccagcatg gacacgttgt tgttcatgac caggccaagc agaaagagca ccaggggtgg    480
cgccagcagg atgcccgcgc tgtaggctgc attgtagccc ggcaggcagg ggcagttgaa    540
gtcgaaggcc gagtacatct gggcactggc cagggccatg atgccacaga tgccattcat    600
gaaggactcc tggttggact gcaggaactg gaagatcatc cggaacttgt ccatcatgcc    660
cgctgtgggg cccggcctcc tcttcccaac tcactgctgc ctccaagagg gcccctgctg    720
cccaccctgc ccactgggtg cccacctcat gactcgggct ctcctggctg ggaccaacag    780
agctcagagc agaggctgag g                                              801
```

METHOD OF SCREENING COMPOUNDS USING CALHM (FAM26C)

This application is a U.S. national phase of PCT Application No. PCT/US08/009,556, filed Aug. 8, 2008, which claims the benefit of U.S. Provisional Application No. 60/964,282, filed Aug. 10, 2007, the content of which is hereby incorporated by reference into the subject application.

BACKGROUND OF THE INVENTION (1) Field of the Invention

The present invention generally relates to genes and proteins that affect diseases in mammals. More specifically, the invention is directed to methods for determining the likelihood that a subject will develop Alzheimer's disease. The invention is also directed to proteins that affect $Ca^{2+}$ transport in cells.

(2) Description of the Related Art

Alzheimer's disease (AD) is a progressive neurodegenerative disorder characterized by a massive brain loss and by the presence of senile plaques and neurofibrillary tangles, two characteristic cerebral lesions formed by the aggregation of Aβ and tau proteins, respectively (Mattson, 2004; Selkoe, 2001). Sequential proteolysis of the amyloid-beta precursor protein (APP) by beta- and gamma-secretases produces two major Aβ species, Aβ40 and Aβ42, and increased Aβ production could represent a key determinant in amyloid formation and thus in the pathogenesis of AD.

The first atrophy observed in the AD brain occurs in the medial temporal lobe, which includes the hippocampus, and is the result of a massive synaptic degeneration and neuronal death (Braak and Braak, 1991). This early neurodegenerative process in the hippocampus is believed to lead to the characteristic learning and memory impairments observed in AD patients (de Leon et al., 2004). The etiology of the disease is complex because of its strong genetic heterogeneity (Marambaud and Robakis, 2005). Rare autosomal dominant mutations in the genes coding for the amyloid precursor protein (APP) and presenilins cause early-onset AD, whereas complex interactions between different genetic variants are believed to modulate the risk for the vast majority of late onset AD (LOAD) cases (Kennedy et al., 2003; Pastor and Goate, 2004). Concordant evidence of linkage to LOAD has been observed in different chromosomal regions, including on chromosome 10 where strong susceptibility loci are present (Kehoe et al., 1999; Bertram et al., 2000; Myers et al., 2000; Ertekin-Taner et al., 2000; Blaker et al., 2003; Farrer et al., 2003). Although significant associations with several candidate genes have been reported within these regions, the only susceptibility gene unambiguously demonstrated worldwide is the ε4 allele of APOE on chromosome 19 (Strittmatter et al., 1993). However, epidemiological studies indicate that the inheritance of the APOE ε4 allele cannot explain the overall heritability of AD, implying that a significant proportion of LOAD cases is attributable to additional genetic risk factors (Pastor and Goate, 2004).

SUMMARY OF THE INVENTION

The present invention is based in part on the discovery that increased risk for Alzheimer's disease is exhibited in individuals having a particular allele of a single nucleotide polymorphism (SNP) present in the FAM26C gene, renamed CALHM1 herein. The inventors have also characterized the CALHM1 protein as a $Ca^{2+}$ ion channel that affects $Ca^{2+}$ homeostasis, as well as Aβ accumulation in APP-transfected cells.

The present invention is directed to methods of determining the likelihood that a subject will be diagnosed with Alzheimer's disease. The methods comprise determining the subject's genotype at SNP rs2986017, where rs2986017 is at position 401 of SEQ ID NO:43. In these methods, an A at both of the subject's SNP rs2986017 alleles indicates an increased likelihood of an Alzheimer's disease diagnosis over a genotype at SNP rs2986017 that comprises a G at both alleles.

The invention is also directed to an isolated and purified mammalian CALHM1 protein, wherein the CALHM1 protein has an amino acid sequence at least 90% identical to SEQ ID NO:17.

Additionally, the invention is directed to a vector comprising a nucleic acid sequence encoding the above CALHM1 protein.

The invention is further directed to a mammalian cell transfected with the above vector.

The invention is additionally directed to an isolated and purified mammalian CALHM2 protein, where the CALHM2 protein has an amino acid sequence at least 90% identical to SEQ ID NO:16.

Also, the invention is directed to a vector comprising a nucleic acid sequence encoding the above CALHM2 protein.

The invention is further directed to a mammalian cell transfected with the above CALHM2 vector.

Additionally, the invention is directed to an isolated and purified mammalian CALHM3 protein, wherein the CALHM3 protein has an amino acid sequence at least 90% identical to SEQ ID NO:15.

The invention is further directed to a vector comprising a nucleic acid sequence encoding the above CALHM3 protein.

Also, the invention is directed to a mammalian cell transfected with the above CALHM3 vector.

The invention is additionally directed to methods of affecting $Ca^{2+}$ levels in a mammalian cell. The methods comprise transfecting the cell with the above-described vector encoding a CALHM1.

The invention is further directed to other methods of affecting $Ca^{2+}$ levels in a mammalian cell. The methods comprise transfecting the cell with the above vector encoding a CALHM2.

The invention is also directed to additional methods of affecting $Ca^{2+}$ levels in a mammalian cell. The methods comprise transfecting the cell with the above vector encoding a CALHM3.

Also, the invention is directed to methods of screening a test compound for the ability to alter calcium homeostasis in a mammalian cell expressing a CALHM1 protein having an amino acid sequence at least 90% identical to SEQ ID NO:17. The methods comprise determining whether the test compound affects expression or activity of the CALHM1 protein. In these methods, a test compound that affects expression or activity of the CALHM1 protein has the ability to alter calcium homeostasis in the mammalian cell.

Additionally, the invention is directed to methods of screening a test compound for the ability to alter calcium homeostasis in a mammalian cell expressing a CALHM2 protein having an amino acid sequence at least 90% identical to SEQ ID NO:16. The methods comprise determining whether the test compound affects expression or activity of the CALHM2 protein. In these methods, a test compound that affects expression or activity of the CALHM2 protein has the ability to alter calcium homeostasis in the mammalian cell.

Further, the invention is directed to methods of screening a test compound for the ability to alter calcium homeostasis in a mammalian cell expressing a CALHM3 protein having an amino acid sequence at least 90% identical to SEQ ID NO:15. The methods comprise determining whether the test compound affects expression or activity of the CALHM3 protein. In these methods, a test compound that affects expression or activity of the CALHM3 protein has the ability to alter calcium homeostasis in the mammalian cell.

The invention is also directed to methods of affecting $Ca^{2+}$ levels in a mammalian cell expressing a CALHM1 protein having an amino acid sequence at least 90% identical to SEQ ID NO:17. The methods comprising contacting the cell with a compound that affects expression or activity of the CALHM1 protein.

The invention is further directed to methods of affecting $Ca^{2+}$ levels in a mammalian cell expressing a CALHM2 protein having an amino acid sequence at least 90% identical to SEQ ID NO:16. The methods comprising contacting the cell with a compound that affects expression or activity of the CALHM2 protein.

The invention is additionally directed to methods of affecting $Ca^{2+}$ levels in a mammalian cell expressing a CALHM3 protein having an amino acid sequence at least 90% identical to SEQ ID NO:15. The methods comprising contacting the cell with a compound that affects expression or activity of the CALHM3 protein.

Also, the invention is directed to methods of screening a test compound for the ability to inhibit ERK1/2 phosphorylation in a mammalian cell. The methods comprise determining whether the test compound affects expression or activity of a CALHM1 protein having an amino acid sequence at least 90% identical to SEQ ID NO:17. In these methods, a test compound that affects expression or activity of the CALHM1 protein has the ability to inhibit ERK1/2 phosphorylation in the mammalian cell.

Additionally, the invention is directed to methods of screening a test compound for the ability to inhibit amyloid-beta peptide accumulation in a mammalian cell or biological fluid. The methods comprise determining whether the test compound affects expression or activity of a CALHM1 protein having an amino acid sequence at least 90% identical to SEQ ID NO:17. In these methods, a test compound that affects expression or activity of the CALHM1 protein may have the ability to inhibit amyloid-beta peptide accumulation in the mammalian cell.

Further, the invention is directed to methods of screening for a test compound that may affect Alzheimer's disease. The methods comprise determining whether the compound affects expression or activity of a CALHM1 protein having an amino acid sequence at least 90% identical to SEQ ID NO:17. In these methods, a test compound that affects expression or activity of the CALHM1 protein may affect Alzheimer's disease.

DETAILED DESCRIPTION OF THE INVENTION

Figure 1:
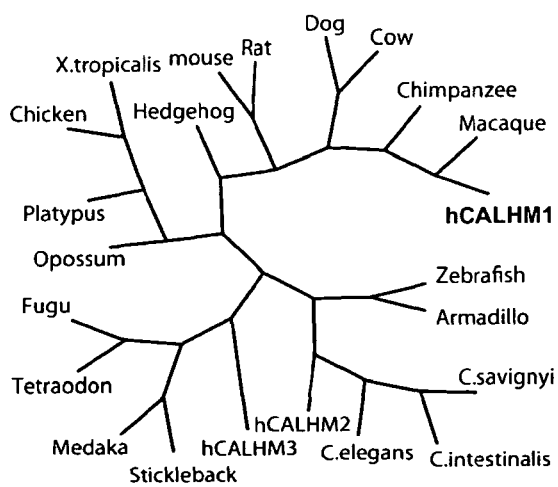
FIG. 1 shows the alignment and phylogeny of CALHM1. Panel a shows a sequence alignment of human CALHM3 (SEQ ID NO:15), CALHM2 (SEQ ID NO:16), and CALHM1 (SEQ ID NO:17), and of murine and *C. elegans* CALHM1 (SEQ ID NO:18 and 19, respectively). Conserved sequences are shaded and sequence conservation is mapped in a shading gradient manner, the darkest shading representing the sequences of absolute identity and lighter shading representing the sequences of weaker conservation. Boxes denote hydrophobic domains 1-4 (HD1-4). * shows predicted N-glycosylation sites on human CALHM1. Panel b shows a phylogenetic tree including human CALHM1 (hCALHM1).

The inventors have discovered that increased risk for Alzheimer's disease is exhibited in individuals having a particular allele of the single nucleotide polymorphism (SNP) rs2986017, which is present in the FAM26C gene, renamed CALHM1 herein (Example 1). The inventors have also characterized the CALHM1 protein, and related proteins CALHM2 and CALHM3 as $Ca^{2+}$ ion channels that affect $Ca^{2+}$ homeostasis (Example 1). Additionally, CALHM1 protein was found to affect Aβ accumulation in APP-transfected cells (Example 2). These discoveries allow prediction of the relative risk of developing Alzheimer's disease. The discoveries also enable the manipulation of $Ca^{2+}$ levels in cells using the CALHM1, CALHM2 and CALHM3 proteins.

The present invention is thus directed to methods of determining the likelihood that a subject will be diagnosed with Alzheimer's disease. The methods comprise determining the subject's genotype at SNP rs2986017, where rs2986017 is at position 401 of SEQ ID NO:43. In these methods, an A at both of the subject's SNP rs2986017 alleles (i.e., homozygous AA genotype at rs2986017) indicates an increased likelihood of an Alzheimer's disease diagnosis over a genotype at SNP rs2986017 that comprises a G at both alleles (i.e., homozygous GG genotype at rs2986017).

As described in Example 1, increased risk for Alzheimer's was conferred to the TT genotype at SNP rs2986017. This corresponds to the opposite strand AA genotype as described in the Genbank SNP database, describing the contig DNA at rs2986017, and provided as SEQ ID NO:43.

Preferably in these methods, an A at both of the subject's SNP rs2986017 alleles (i.e., AA homozygote) indicates an increased likelihood of an Alzheimer's disease diagnosis over a genotype at SNP rs2986017 that comprises a G at one or both alleles (i.e., GA heterozygote or GG homozygote). More preferably, an A at one or both of the subject's SNP rs2986017 alleles (i.e., AG heterozygote or AA homozygote) indicates an increased likelihood of an Alzheimer's disease diagnosis over a genotype at SNP rs2986017 that comprises a G at both alleles (i.e., GG homozygote).

The patient's genotype at rs2986017 can be linked to other SNPs, such that the genotype of the two SNPs are in linkage disequilibrium (LD) to each other. When the two SNPs are in LD, the two SNPs do not assort independently as in Hardy-Weinberg equilibrium (Balding, 2006). Under LD, the two SNPs are linked such that the prediction of the genotype at one SNP can be more and more reliably determined as LD increases by determining the genotype at the linked SNP. Thus, the genotype at a selected SNP can be reliably determined by determining the genotype at a SNP that is at high LD with the selected SNP.

The most common measures of LD are D' and $r^2$ (Balding, 2006). With both of these measures, LD increases as D' and $r^2$ approach 1.0. Thus, in these methods, the genotype at the selected SNP can be determined by determining the genotype at a second SNP that is at a high level of LD with the selected SNP.

In these methods, the patient's genotype at rs2986017 can thus be determined by determining the genotype at a secondary single nucleotide polymorphism (SNP) in linkage disequilibrium to rs2986017. Here, the linkage disequilibrium measure D' between rs2986017 and the secondary SNP is greater than about 0.70, preferably greater than about 0.80, and more preferably greater than about 0.90 or 0.95 or 0.99.

The patient's genotype at rs2986017 can also be determined by determining the genotype at a secondary single nucleotide polymorphism (SNP) in linkage disequilibrium to rs2986017, where the linkage disequilibrium measure $r^2$ between rs2986017 and the secondary SNP is greater than about 0.50, preferably greater than about 0.80, and more preferably greater than about 0.90 or 0.95 or 0.99.

The invention is also directed to an isolated and purified mammalian CALHM1 protein, wherein the CALHM1 protein has an amino acid sequence at least 90% identical to SEQ ID NO:17. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

The CALHM1 protein here can be from any mammalian species, including rats, mice, or humans. The protein can also comprise a mutation or mutations that alter the protein's amino acid sequence, provided the resulting protein still retains $Ca^{2+}$ ion channel activity.

Additionally, the invention is directed a vector comprising a nucleic acid sequence encoding the above CALHM1 protein. As used herein, a "vector" is a vehicle for delivering genetic material to a cell. The invention is not narrowly limited to any particular type of vector, Any such vector now known or later discovered may be utilized here, including, but not limited to, a plasmid vector or a viral vector. The skilled artisan would be capable of selecting the preferred vector for any particular purpose without undue experimentation. Preferably, the vector expresses the CALHM1 protein when transfected into a mammalian cell.

The invention is further directed to a mammalian cell transfected with the above vector. The cell here can be from any mammalian species, including rats and mice. Preferably, the cell is a human cell. The cell can be in culture, or preferably, the cell is in a living mammal.

The mammalian cell of these embodiments can be from any tissue type, including cells that naturally express CALHM1 and cells that do not. Preferably, the cell is a nerve cell or a brain cell. A preferred brain cell is a hippocampal cell. Other preferred cells are a spinal cord cell, a cerebral cortex cell, a cerebellum cell, a temporal lobe cell, a frontal lobe cell, and an occipital pole cell.

The invention is additionally directed to an isolated and purified mammalian CALHM2 protein, where the CALHM2 protein has an amino acid sequence at least 90% identical to SEQ ID NO:16. Preferably, the CALHM2 protein has an amino acid sequence at least 99% identical to SEQ ID NO:16.

More preferably, the CALHM2 protein has an amino acid sequence completely identical to SEQ ID NO:16.

Also, the invention is directed a vector comprising a nucleic acid sequence encoding the above CALHM2 protein. Preferably, the vector expresses the CALHM2 protein when transfected into a mammalian cell.

The invention is further directed to a mammalian cell transfected with the above CALHM2 vector. The cell here can be from any mammalian species, including rats and mice. Preferably, the cell is a human cell. The cell can be in culture, or preferably, the cell is in a living mammal.

The mammalian cell of these embodiments can be from any tissue type, including cells that naturally express CALHM2 and cells that do not. Preferably, the cell is a brain cell, a uterine cell or a heart cell.

Additionally, the invention is directed to an isolated and purified mammalian CALHM3 protein, wherein the CALHM3 protein has an amino acid sequence at least 90% identical to SEQ ID NO:15. Preferably, the CALHM3 protein has an amino acid sequence at least 99% identical to SEQ ID NO:15. More preferably, the CALHM23 protein has an amino acid sequence completely identical to SEQ ID NO:15.

Also, the invention is directed a vector comprising a nucleic acid sequence encoding the above CALHM3 protein. Preferably, the vector expresses the CALHM3 protein when transfected into a mammalian cell.

The invention is further directed to a mammalian cell transfected with the above CALHM3 vector. The cell here can be from any mammalian species, including rats and mice. Preferably, the cell is a human cell. The cell can be in culture, or preferably, the cell is in a living mammal.

The mammalian cell of these embodiments can be from any tissue type, including cells that naturally express CALHM3 and cells that do not. Preferably, the cell is a placental cell.

The invention is additionally directed to methods of affecting $Ca^{2+}$ levels in a mammalian cell. The methods comprise transfecting the cell with the above-described vector encoding a CALHM1.

The cell here can be from any mammalian species, including rats and mice. Preferably, the cell is a human cell. The cell can be in culture, or preferably, the cell is in a living mammal. The mammalian cell of these embodiments can be from any tissue type, including cells that naturally express CALHM1 and cells that do not.

The invention is further directed to methods of affecting $Ca^{2+}$ levels in a mammalian cell. The methods comprise transfecting the cell with the above vector encoding a CALHM2.

The cell here can be from any mammalian species, including rats and mice. Preferably, the cell is a human cell. The cell can be in culture, or preferably, the cell is in a living mammal. The mammalian cell of these embodiments can be from any tissue type, including cells that naturally express CALHM2 and cells that do not.

The invention is also directed to methods of affecting $Ca^{2+}$ levels in a mammalian cell. The methods comprise transfecting the cell with the above vector encoding a CALHM3.

The cell here can be from any mammalian species, including rats and mice. Preferably, the cell is a human cell. The cell can be in culture, or preferably, the cell is in a living mammal. The mammalian cell of these embodiments can be from any tissue type, including cells that naturally express CALHM3 and cells that do not.

Also, the invention is directed to methods of screening a test compound for the ability to alter calcium homeostasis in a mammalian cell expressing a CALHM1 protein having an amino acid sequence at least 90% identical to SEQ ID NO:17. The methods comprise determining whether the test compound affects expression or activity of the CALHM1 protein. In these methods, a test compound that affects expression or activity of the CALHM1 protein has the ability to alter calcium homeostasis in the mammalian cell. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

Expression or activity of the CALHM1 protein can be determined by any method known in the art. For example, expression can be determined by determining levels of CALHM1 mRNA in the cell (e.g., by RT-PCR) or by quantifying the CALHM1 protein (e.g., by ELISA or western blot). Activity of the CALHM1 protein can be determined, e.g., by the methods described in Example 1.

These methods are not limited to testing any particular type of test compound. In some aspects, the test compound is a nucleic acid. An example is an aptamer that specifically binds to the CALHM1 protein. Preferably, the nucleic acid is complementary to a portion of the gene encoding the CALHM1 protein, e.g., an RNAi molecule (i.e., an miRNA, or any other small double-stranded RNA, now known or later discovered, that is capable of specifically interfering with expression of the target gene), an antisense molecule or a ribozyme.

The test compound in these methods can alternatively be a polypeptide, for example a protein that specifically binds to the CALHM1, preferably activating ion channel function. A preferred polypeptide test compound for these methods comprises an antibody binding site (e.g., a monoclonal antibody).

The test compound for these methods can also be an organic molecule less than about 1000 mw.

Additionally, the invention is directed to methods of screening a test compound for the ability to alter calcium homeostasis in a mammalian cell expressing a CALHM2 protein having an amino acid sequence at least 90% identical to SEQ ID NO:16. The methods comprise determining whether the test compound affects expression or activity of the CALHM2 protein. In these methods, a test compound that affects expression or activity of the CALHM2 protein has the ability to alter calcium homeostasis in the mammalian cell. Preferably, the CALHM1 protein has an amino acid sequence at least 99% identical to SEQ ID NO:16. More preferably, the CALHM1 protein has an amino acid sequence completely identical to SEQ ID NO:16.

Further, the invention is directed to methods of screening a test compound for the ability to alter calcium homeostasis in a mammalian cell expressing a CALHM3 protein having an amino acid sequence at least 90% identical to SEQ ID NO:15. The methods comprise determining whether the test compound affects expression or activity of the CALHM3 protein. In these methods, a test compound that affects expression or activity of the CALHM3 protein has the ability to alter calcium homeostasis in the mammalian cell. Preferably, the CALHM1 protein has an amino acid sequence at least 99% identical to SEQ ID NO:15. More preferably, the CALHM1 protein has an amino acid sequence completely identical to SEQ ID NO:15.

The invention is also directed to methods of affecting $Ca^{2+}$ levels in a mammalian cell expressing a CALHM1 having an amino acid sequence at least 90% identical to SEQ ID NO:17. The methods comprise contacting the cell with a compound that affects expression or activity of the CALHM1 protein. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

These methods are not limited to the use of any particular type of compound that affects expression or activity of the CALHM1 protein. In some aspects, the compound affects expression of the CALHM1 protein. Preferred such compounds are complementary to a portion of the gene encoding the CALHM1 protein and include an antisense molecule, a ribozyme or an RNAi molecule. Another preferred compound that affects the expression of the CALHM1 protein is the vector described above that expresses the CALHM1 protein when transfected into a mammalian cell. Such a vector would increase expression of the CALHM1 protein.

In other aspects of these methods, the compound affects activity of the CALHM1 protein. Preferred such compounds comprise an antibody binding site, e.g., a monoclonal antibody that specifically binds to the CALHM1 protein, preventing $CA^{2+}$ ion transport. The compound can also be an aptamer, e.g., that also specifically binds to the CALHM1 protein, preventing $CA^{2+}$ ion transport. The compound can alternatively be an organic molecule less than about 1000 mw. In some embodiments, the compound used was identified by the above-described method of screening a test compound for the ability to alter calcium homeostasis in a mammalian cell expressing a CALHM1 protein.

The invention is further directed to methods of affecting $Ca^{2+}$ levels in a mammalian cell expressing a CALHM2 protein having an amino acid sequence at least 90% identical to SEQ ID NO:16. The methods comprise contacting the cell with a compound that affects expression or activity of the CALHM2 protein. Preferably, the CALHM2 protein has an amino acid sequence at least 99% identical to SEQ ID NO:16. More preferably, the CALHM2 protein has an amino acid sequence completely identical to SEQ ID NO:16.

The invention is additionally directed to methods of affecting $Ca^{2+}$ levels in a mammalian cell expressing a CALHM3 protein having an amino acid sequence at least 90% identical to SEQ ID NO:15. The methods comprise contacting the cell with a compound that affects expression or activity of the CALHM3 protein. Preferably, the CALHM3 protein has an amino acid sequence at least 99% identical to SEQ ID NO: 15. More preferably, the CALHM3 protein has an amino acid sequence completely identical to SEQ ID NO:15.

Also, the invention is directed to methods of screening a test compound for the ability to inhibit ERK1/2 phosphorylation in a mammalian cell. The methods comprise determining whether the test compound affects expression or activity of a CALHM1 protein having an amino acid sequence at least 90% identical to SEQ ID NO:17. In these methods, a test compound that affects expression or activity of the CALHM1 protein has the ability to inhibit ERK1/2 phosphorylation in the mammalian cell. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

These methods are not limited to testing any particular type of test compound. In some aspects, the test compound is a nucleic acid. An example is an aptamer that specifically binds to the CALHM1 protein. Preferably, the nucleic acid is complementary to a portion of the gene encoding the CALHM1 protein, e.g., an RNAi molecule, an antisense molecule or a ribozyme.

The test compound in these methods can alternatively be a polypeptide, for example a protein that specifically binds to the CALHM1, preferably activating ion channel function. A preferred polypeptide test compound for these methods comprises an antibody binding site (e.g., a monoclonal antibody). The test compound for these methods can also be an organic molecule less than about 1000 mw.

Additionally, the invention is directed to methods of screening a test compound for the ability to inhibit amyloid-beta peptide accumulation in a mammalian cell or biological fluid. The methods comprise determining whether the test compound affects expression or activity of a CALHM1 protein having an amino acid sequence at least 90% identical to SEQ ID NO:17. In these methods, a test compound that affects expression or activity of the CALHM1 protein may have the ability to inhibit amyloid-beta peptide accumulation in the mammalian cell. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

These methods are not limited to testing any particular type of test compound. In some aspects, the test compound is a nucleic acid. An example is an aptamer that specifically binds to the CALHM1 protein. Preferably, the nucleic acid is complementary to a portion of the gene encoding the CALHM1 protein, e.g., an RNAi molecule, an antisense molecule or a ribozyme.

The test compound in these methods can alternatively be a polypeptide, for example a protein that specifically binds to the CALHM1, preferably activating ion channel function. A preferred polypeptide test compound for these methods comprises an antibody binding site (e.g., a monoclonal antibody). The test compound for these methods can also be an organic molecule less than about 1000 mw.

Further, the invention is directed to methods of screening for a test compound that may affect Alzheimer's disease. The methods comprise determining whether the compound affects expression or activity of a CALHM1 protein having an amino acid sequence at least 90% identical to SEQ ID NO:17. In these methods, a test compound that affects expression or activity of the CALHM1 protein may affect Alzheimer's disease. Preferably, the CALHM1 protein has an amino acid sequence at least 99% identical to SEQ ID NO:17. More preferably, the CALHM1 protein has an amino acid sequence completely identical to SEQ ID NO:17. In some embodiments, the CALHM1 protein has an amino acid sequence completely identical to SEQ ID NO:17 except for an L86P substitution.

These methods are not limited to testing any particular type of test compound. In some aspects, the test compound is a nucleic acid. An example is an aptamer that specifically binds to the CALHM1 protein. Preferably, the nucleic acid is complementary to a portion of the gene encoding the CALHM1 protein, e.g., an RNAi molecule (e.g., an miRNA, or any other small double stranded RNA, now known or later discovered, that is capable of specifically interfering with expression of the target gene), an antisense molecule or a ribozyme.

The test compound in these methods can alternatively be a polypeptide, for example a protein that specifically binds to the CALHM1, preferably activating ion channel function. A preferred polypeptide test compound for these methods comprises an antibody binding site (e.g., a monoclonal antibody). The test compound for these methods can also be an organic molecule less than about 1000 mw.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

A Variant in CALHM1 Influences $Ca^{2+}$ Homeostasis and Alzheimer Disease Risk

Example Summary

DbEST was mined with TissueInfo for screening genes preferentially expressed in the hippocampus and located in linkage regions for Alzheimer disease. Reported here is the identification and characterization of CALHM1 on chromosome 10 that encodes a novel integral membrane glycoprotein controlling cytosolic $Ca^{2+}$ levels and ERK/1/2 activation. CALHM1 was found to form homomultimers and to share striking sequence similarities with the ion selectivity filter of NMDA receptor. The conserved and functionally critical N72 residue in CALHM1 that aligns with the Q/R/N site of MNDA receptor was further identified. The common polymorphism P86L in CALHM1 caused impairments in $Ca^{2+}$ homeostasis and was significantly over-represented in Alzheimer disease subjects in a large French case-control population. These data provide strong evidence that CALHM1 encodes an essential pore component of a novel ion channel family and constitutes a susceptibility gene for Alzheimer disease.

Introduction

Some neurodegenerative disorders are caused by mutations in genes almost exclusively expressed in the central nervous system. For instance, mutations in the brain proteins tau and α-synuclein, lead to autosomal dominant forms of frontotemporal dementia (Dermaut et al., 2005) and Parkinson's disease (Lee and Trojanowski, 2006), respectively. In this context, it was hypothesized that susceptibility for LOAD may come from genes predominantly expressed in affected brain regions, such as the hippocampus. By using TissueInfo (Skrabanek and Campagne, 2001) and the Alzgene database (Bertram et al., 2007) to screen for genes predominantly expressed in the hippocampus and located in linkage regions for LOAD, CALHM1 was identified. CALHM is designated a gene of unknown function, located on chromosome 10 at 1.6 Mb of the LOAD marker D10S1671 (Bertram et al., 2000). CALHM1 together with its two homologs, CALHM2 and CALHM3, represent the CALHM gene family and are clustered in 10q24.33. This work describes studies that show that CALHM1 homomultimerizes, controls cytosolic $Ca^{2+}$ homeostasis, and shares similarities with the predicted selectivity filter of N-methyl-D-aspartate receptor (NMDAR). Importantly, it was also determined that the non-synonymous single nucleotide polymorphism (SNP) rs2986017 in CALHM1, which results in the P86L substitution, causes robust impairments in the regulation of cytosolic $Ca^{2+}$ levels and in ERK1/2 phosphorylation. Further investigation determined that the frequency of the functional P86L polymorphism is significantly increased in a large cohort of AD cases in the French population. Here, it is proposed that CALHM1 is a pore component of a novel ion channel family of the brain and that variants in its gene family may constitute risk factors for LOAD. These results not only provide important new insights into the pathophysiology of cerebral $Ca^{2+}$ homeostasis but also represent the first genetic evidence for a channelopathy component in AD etiology.

Results

Gene discovery. The human genome was screened with TissueInfo to annotate human transcripts with tissue expression levels derived from the expressed sequence tag database (dbEST) (Skrabanek and Campagne, 2001; Campagne and Skrabanek, 2006). Out of 33,249 human transcripts, the TissueInfo screen identified 30 transcripts whose expression was restricted to the hippocampus. These transcripts matched one to four ESTs sequenced from the hippocampus. Among these genes, a gene of unknown function previously annotated as FAM26C (Schneeberger et al., 2005) mapped to the AD locus on chromosome 10q and matched two hippocampal ESTs. This gene is hereafter referred to as CALHM1 (calcium homeostasis modulator 1). CALHM1 encodes an open reading frame of 346 amino acids predicted to contain four hydrophobic domains (HDs; TMHMM prediction) (Sonnhammer et al., 1998) and two N-glycosylation motifs (NetNGlyc 1.0 prediction) (Gupta and Jung, 2007) (FIG. 1A). No significant amino acid sequence homology to other functionally characterized proteins was found. Sequence database searches, however, identified five human homologs of CALHM1 (collectively identified as the FAM26 gene family) (Schneeberger et al., 2005). Two homologs of human CALHM1 are located next to CALHM1 on chromosome 10 and are designated CALHM2 (26% protein sequence identity) and CALHM3 (39% identity) (Schneeberger et al., 2005). CALHM1 is conserved across at least 20 species including mouse and *C. elegans* (see FIGS. 1A and 1B).

Figure 2:
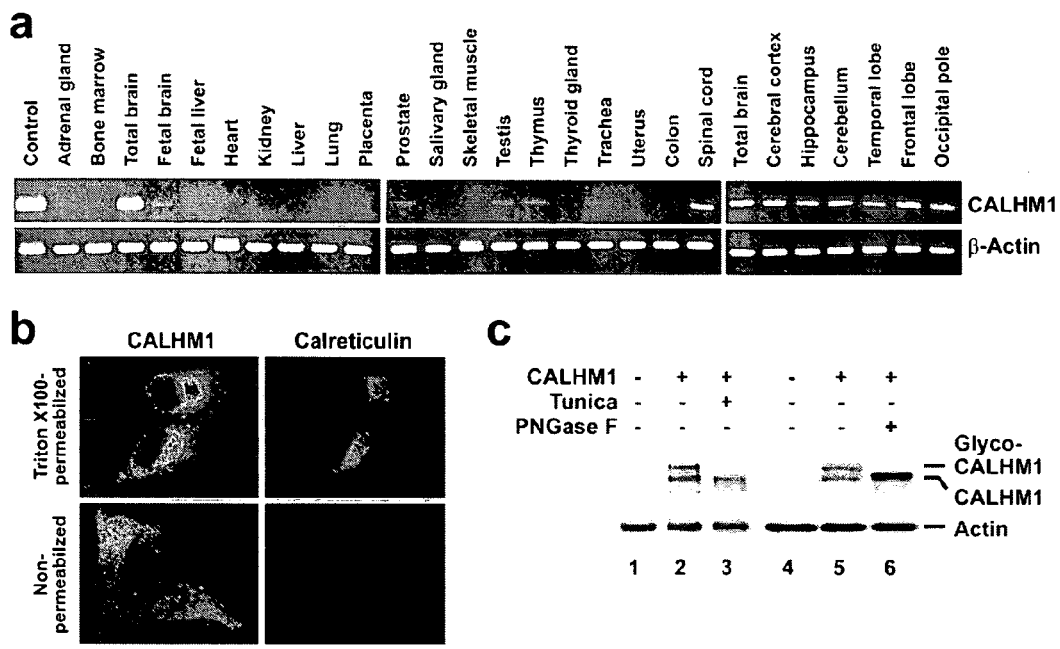
FIG. 2 is photographs of gels and western blots (WBs) and fluorescent micrographs of cells showing tissue expression, subcellular localization, and N-glycosylation of human CALHM1. For Panel a, total RNA was used for RT-PCR analyses targeting CALHM1 and β-actin transcripts in multiple human tissues (the first 20 lanes) and brain regions (the remaining 7 lanes on the right). Panel b shows immunofluorescence staining of permeabilized or non-permeabilized HT-22 cells transfected with human Myc-tagged CALHM1 (Myc-CALHM1) using anti-Myc (green) and anti-calreticulin (red) antibodies. Panel c shows HEK293 (lanes 1-3) and HT-22 (lanes 4-6) cells transfected with Myc-CALHM1 after incubation in the absence (−) or presence (+) of tunicamycin (Tunica) or N-glycosidase F (PNGase F). Lysates were probed with anti-Myc (upper panels) and anti-actin antibodies.

CALHM1 characterization. Using RT-PCR, we analyzed human CALHM1 gene expression in 20 tissues and six brain regions. The expression of CALHM1 was highest in the total adult brain and in all brain regions tested (FIG. 2A). CALHM1 expression was noticeably lower in all other tissues including fetal brain. No expression was detected in liver, heart, kidney, placenta, skeletal muscle, and uterus (FIG. 2A). Immunofluorescence staining in transiently transfected cells revealed that CALHM1 localizes predominantly to the endoplasmic reticulum (ER) where it colocalizes with the ER marker calreticulin (FIG. 2B). Immunofluorescence staining in non-permeabilized conditions revealed, however, the presence of several cells immunoreactive for CALHM1, indicating that a small pool of the protein reaches the cell surface (FIG. 2B). These data further show that the C-terminus end of the CALHM1 is extracellutarly oriented and so accessible to the anti-Tag antibody (FIG. 2B). Western blotting analyses revealed the presence of two immunoreactive bands in CALHM1-transfected cells (FIG. 2C, lanes 2 and 5). Because CALHM1 is predicted to be N-glycosylated, it was asked whether these bands might represent different N-glycosylated forms of the protein. It was found that treatment with tunicamycin, which blocks cotranslational N-glycosylation within the ER, completely inhibited the appearance of the band of higher molecular weight and resulted in the maintenance of the lower band corresponding, therefore, to the unmodified core-protein (FIG. 2C, lanes 1-3). In vitro treatments of CALHM1-transfected cell lysates with N-glycosidase F, which cleaves all types of asparagine bound N-glycans, also resulted in a molecular weight switch characteristic of protein deglycosylation (FIG. 2C, lanes 4-6). Thus, CALHM1 is a multipass transmembrane glycoprotein predominantly expressed in the adult brain and localized to the ER and plasma membranes.

CALHM1 controls cytosolic $Ca^{2+}$ levels and ERK1/2 phosphorylation. TMHMM predicts that HD3 in CALHM1 is a re-entrant hydrophobic loop that does not cross the membrane bilayer, whereas HD1, HD2, and HD4 are membrane-spanning segments (Sonnhammer et al., 1998). In the absence of significant homology to other characterized proteins, it was postulated from the predicted topology that CALHM1 could represent an ion channel component. A suggestive similarity was indeed observed with the topology of ionotropic glutamate receptors, which also contain three transmembrane segments and a re-entrant loop that forms the lining of the pore region of the ion channels (Wollmuth and Sobolevsky, 2004). Because ionotropic glutamate receptors are $Ca^{2+}$-transport membrane proteins (Gouaux and Mackinnon, 2005), it was asked whether CALHM1 could control cytoplasmic $Ca^{2+}$ levels. Using Fluo-4 measurements in mouse hippocampal HT-22 cells, it was determined that transient expression of CALHM1 resulted in a robust and sustained increase in intracellular $Ca^{2+}$ concentration ($[Ca^{2+}]_i$) under extracellular "$Ca^{2+}$ add-back" conditions (FIG. 3A). CALHM1 expression significantly increased the initial rate of change in $[Ca^{2+}]_i$ by forming a peak of fluorescence at ~2 min following extracellular $Ca^{2+}$ addition (FIGS. 3A and 3B, Peak). Expression of CALHM1 also induced a significant elevation in the steady-state $[Ca^{2+}]_i$, as compared to control conditions (FIG. 3B, Steady-state).

Cytosolic $Ca^{2+}$ originates from the extracellular space or from intracellular stores, such as the ER (Berridge et al., 2003). $Ca^{2+}$ release from the ER is mediated by ion channels, such as the inositol 1,4,5-triphosphate receptors ($InsP_3Rs$) or the ryanodine receptors (RyRs) (Id), whereas plasma membrane ion channels control $Ca^{2+}$ influx. One important pathway of $Ca^{2+}$ entry is coupled to ER $Ca^{2+}$ release and is mediated by the mechanism of store operated $Ca^{2+}$ entry (SOCE) (Lewis, 2007). We found that $InsP_3R$, RyR, or SOCE inhibitors had no effect on the $[Ca^{2+}]_i$ increase by CALHM1 (FIGS. 3C and 3D), indicating that CALHM1 does not promote $Ca^{2+}$ influx or ER $Ca^{2+}$ release by facilitating SOCE or activating $InsP_3Rs$ and RyRs.

To address the physiological relevance of this observation, it was then asked whether CALHM1 expression could promote a $Ca^{2+}$-dependent signaling pathway. Cytosolic $Ca^{2+}$ is a remarkably versatile signal that controls multiple kinase-mediated pathways (Id.). ERK1/2 (extracellular signal-regulated kinases-1 and -2) became the focus because those kinases are involved in synaptic signaling in the adult brain and in the formation of long-term memories (Thomas and Huganir, 2004). Mechanistically, ERK1/2 are activated by phosphorylation by MEK1/2 (mitogen-activated protein kinase kinases-1 and -2) upon NMDAR-mediated $Ca^{2+}$ influx during synaptic stimulation (Id). It was found that CALHM1 transient expression induced a robust increase in phosphorylated ERK1/2 (pERK1/2) levels under "$Ca^{2+}$ add-back" conditions (FIG. 3E). This CALHM1-dependent increase in pERK1/2 was blocked by a MEK1/2 inhibitor and by intracellular $Ca^{2+}$ chelation (FIG. 3E), showing that the stimulatory effect of CALHM1 on pERK1/2 is mediated by MEK1/2 and is dependent on $Ca^{2+}$. Thus, CALHM1 promotes ERK1/2 phosphorylation by increasing $[Ca^{2+}]_i$ and activating MEK1/2.

CALHM1 has ion channel properties. Because many channels multimerize to form the ion pore (Ashcroft, 2006), and because monomeric CALHM1 cannot create a functional pore with three transmembrane segments, it was asked whether CALHM1 could form multimers. Western blot analysis of CALHM1-transfected cells under non-reducing conditions revealed the presence of immunoreactive bands with high molecular weights compatible with dimers and tetramers of CALHM1 (FIG. 4A). To test the possibility that CALHM1 self-associates, two differently tagged versions of the protein were co-expressed and co-immunoprecipitation experiments were undertaken to determine whether the two versions of CALHM1 form a complex. It was found that immunoprecipitation of a Myc-tagged CALHM1 co-precipitated with a V5-tagged CALHM1 (FIG. 4B), indicating that CALHM1 indeed homomultimerizes to form dimeric and possibly tetrameric structures.

Ionotropic glutamate receptors are ion-transport membrane proteins that operate in a selectively manner (Gouaux and Mackinnon, 2005). Recent advances made in the structural analysis of some ion channels have determined that ion selectivity is controlled by a short amino acid sequence called selectivity filter, which forms a narrow constriction in the pore across the membrane bilayer (Gouaux and Mackinnon, 2005; Doyle et al., 1998). The predicted selectivity filter of ionotropic glutamate receptors is located in the re-entrant loop called M2 and is critical for $Ca^{2+}$ permeability (Wollmuth and Sobolevsky, 2004; Dingledine et al., 1999). By manual inspection, ionotropic glutamate receptor subunit sequences were screened for similarities with CALHM1. A short sequence was found in the C-terminus of CALHM1 HD2 that aligns with the predicted ion selectivity filter of NMDAR NR2 subunits (FIG. 4C). Previous studies have determined that the asparagine (N) residue in the so-called Q/R/N site of NMDAR NR2 subunits is critical for ion selectivity and permeation (see FIG. 4C, *) (Wollmuth and Sobolevsky, 2004). By sequence comparison, the highly conserved N72 residue was identified in human CALHM1 that aligns with the Q/R/N site at the C-terminus end of the second hydrophobic domain of both CALHM1 and NMDAR (FIG. 4C, *). Importantly, it was found that mutagenesis of the N72 residue to glycine (N72G) resulted in a significant inhibition of the effect of CALHM1 on $[Ca^{2+}]_i$ (FIGS. 4D, E). Hence, CALHM1 shares striking similarities with the selectivity filter of NMDAR and the N72 residue is a key determinant in the control of cytosolic $Ca^{2+}$ levels by CALHM1. Together with the observation that the effect of CALHM1 does not implicate known $Ca^{2+}$ channels, these results strongly support the notion that CALHM1 is a novel pore-forming ion channel.

The CALHM1 P86L polymorphism is associated with LOAD. Because CALHM1 maps to a susceptibility region for LOAD, it was next tested whether CALHM1 SNPs are associated with LOAD. Two non-synonymous SNPs were already reported in databases, rs2986017 (+394 C/T; P86L) and rs17853566 (+927 C/A; H264N). CALHM1 exons were first sequenced in genomic DNA of 37 individuals, including 24 autopsy-confirmed AD cases and 13 age-matched normal controls. The rs17853566 SNP was not observed in this group. However, the presence of rs2986017 was confirmed (genotype distribution: CC=49%; CT=38%; TT=13%), with a potential over-representation of the TT genotype in AD subjects (AD=16.7%; Control=7.7%). In order to confirm this observation obtained in a very small sample, the impact of the rs2986017 SNP on the risk of developing LOAD was next assessed in a large French case-control population (710 LOAD cases and 565 controls, Table 1). The SNP distribution was in Hardy-Weinberg equilibrium in the control population ($\chi^2$=2.3; Table 1) but not in LOAD cases ($\chi^2$=15.1; Table 1). Importantly, the T allele distribution was significantly increased in LOAD cases (26%) as compared to controls (20%; P=0.0002; odds ratio=1.4). In addition, the TT genotype was found at a significantly higher frequency in LOAD subjects (10%) as compared to controls (5%; P=0.002; odds ratio=2.2; Table 1). The CALHM1 rs2986017 SNP is therefore significantly associated with an increased risk for AD in the French population tested. Consistently, we noticed that the patients bearing the TT genotype had an earlier age at onset compared with the CT and CC carriers (66.8±8.5 versus 68.7±7.7; P=0.05). In order to gain insight into the relevance of the rs2986017 SNP for the disease, the effect of the corresponding P86L substitution on $Ca^{2+}$ homeostasis was investigated. Importantly, it was observed that the P86L mutation caused a significant inhibition of the effect of CALHM1 both on $[Ca^{2+}]_i$ (FIGS. 5A and 5B) and on ERK1/2 phosphorylation (FIG. 5C).

TABLE 1

Allele and genotype distribution of the CALHM1 P86L polymorphism in AD case and control populations

|  | n | Allele distribution (%)[1] | | Genotype distribution (%)[2] | | |
| --- | --- | --- | --- | --- | --- | --- |
|  |  | C | T | CC | CT | TT |
| AD cases | 710 | 1051 (0.74) | 369 (0.26) | 410 (0.58) | 231 (0.32) | 69 (0.10) |
| Control | 565 | 907 (0.80) | 223 (0.20) | 370 (0.65) | 167 (0.30) | 28 (0.05) |

Figure 3:
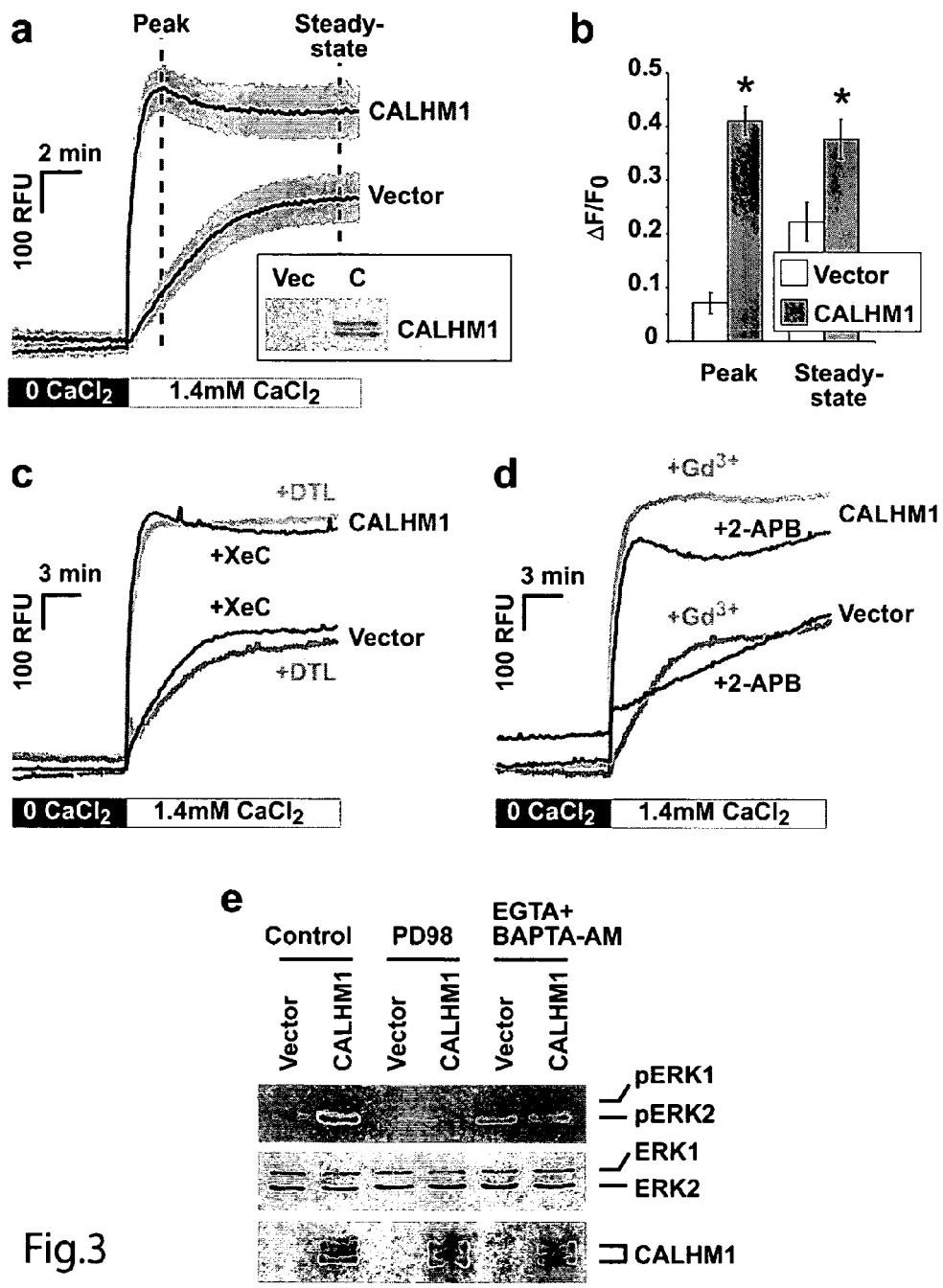
FIG. 3 is graphs and photographs of WBs showing that CALHM1 controls $Ca^{2+}$ homeostasis by a mechanism that does not promote SOCE or activation of InsP$_3$Rs and RyRs. Panel a shows cytoplasmic $Ca^{2+}$ measurements using Fluo-4 loading and "$Ca^{2+}$ add-back" assays in HT-22 cells transiently transfected with Myc-CALHM1 or control vector. Cells were first incubated in $Ca^{2+}$-free buffer (0 $CaCl_2$) and then challenged with physiological extracellular $Ca^{2+}$ concentrations (1.4 mM $CaCl_2$) to monitor the progressive restoration of basal $[Ca^{2+}]_i$. The traces show the mean relative fluorescence units (RFU)+/−S.D. of three independent experiments. Insert, WB of the corresponding cell lysates probed with anti-Myc antibody; Vec, vector; C, CALHM1. Panel b shows peak and steady-state $[Ca^{2+}]_i$ measurements as in Panel a expressed in $\Delta F/F_0$; *, P<0.001 (Student's t test). Panels c and d show cytoplasmic $Ca^{2+}$ measurements as in Panel a in cells pretreated with the RyR inhibitor dantrolene [DTL, 10 µM (C)], the InsP$_3$R inhibitor xestospongin C [XeC, 2 µM (c)], and the two SOCE blockers 2-APB (50 µM) and $Gd^{3+}$ (5 µM) (d). Panel e is WBs from "$Ca^{2+}$ add-back" assays in vector- or Myc-CALHM1-transfected HT-22 cells preincubated in the absence (Control) or presence of PD98059 (PD98, 20 µM), EGTA (2 mM), and BAPTA-AM (20 µM). Cells were exposed to $CaCl_2$ for 30 min. Cell lysates were probed with antibodies directed against phosphorylated ERK1/2 (pERK1/2), total ERK1/2 (ERK1/2), and Myc (lower panels). To prevent rapid dephosphorylation by protein phosphatases, experiments were carried out in the presence of forskolin (30 µM) (Makhinson et al., 1999).
Figure 4:
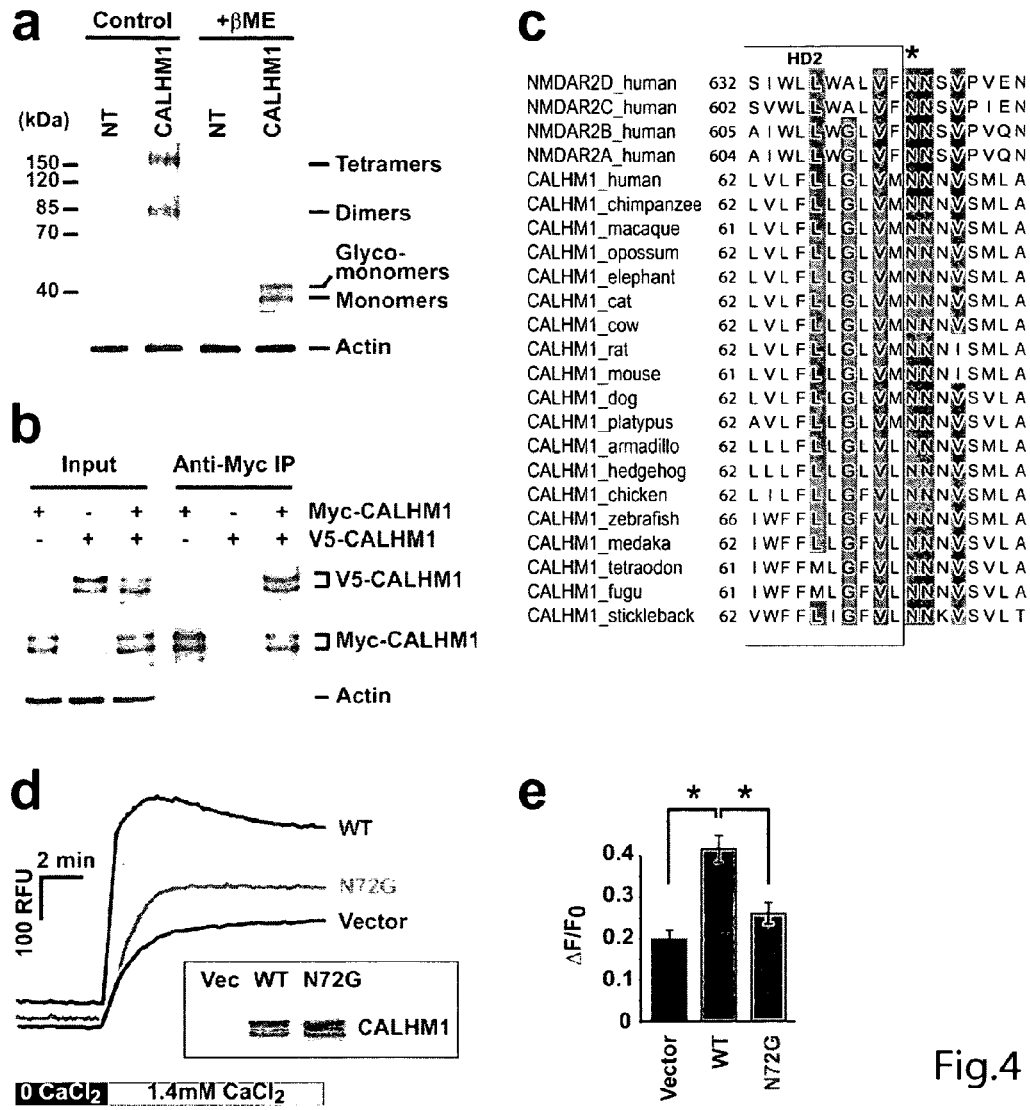
FIG. 4 is a sequence alignment diagram, photographs of WBs and graphs, showing pore-forming properties of CALHM1. Panel a shows WBs of lysates from non-transfected (NT) and Myc-CALHM1-tranfected HEK293 cells in the absence (Control) or presence of β-mercaptoethanol (βME) using anti-Myc (two upper panels) and anti-actin antibodies. Panel b shows WBs of lysates from HEK293 cells transfected (+) or not (−) with V5-tagged CALHM1 (V5-CALHM1) or Myc-CALHM1, after immunoprecipitatation with anti-Myc antibody. Total lysates (Input, left panels) and immunoprecipitates (Anti-Myc IP, right panels) were analyzed by WB using antibodies against V5 (upper panels), Myc (middle panels), and actin. Panel c shows a partial sequence alignment of human NMDAR NR2 (NMDAR2) subunits A-D and CALHM1 from various species. Sequence conservation is highlighted in a shading gradient as described above for FIG. 1A. * denotes Q/R/N site. The sequences, from top to bottom, are SEQ ID NO:20-42, respectively. Panel d shows cytoplasmic $Ca^{2+}$ measurements in HT-22 cells transfected with control vector and wild type (WT) or N72G mutated Myc-CALHM1. Cells were treated and results analyzed as in FIG. 3A (n=3 independent experiments). Insert, WB of the corresponding cell lysates with anti-Myc antibody. Panel e shows peak $[Ca^{2+}]_i$ measurements as in Panel d, expressed in $\Delta F/F_0$; *, P<0.001 (Student's t test).

[1] P = 0.0002;
[2] P = 0.001
OR (T allele versus C allele) = 1.4, 95% CI [1.2-1.7], P = 0.0002
OR (CT + TT versus CC) = 1.4, 95% CI [1.1-1.8], P = 0.007 adjusted on age, gender and APOE status
OR (CT versus CC) = 1.3, 95% CI [1.0-1.7], P = 0.08 adjusted on age, gender and APOE status
OR (TT versus CC) = 2.2, 95% CI [1.3-3.6], P = 0.002 adjusted on age, gender and APOE status Discussion By tissue-specific data mining to screen for genes predominantly expressed in the hippocampus and located in linkage regions for LOAD, CALHM1, on chromosome 10, was identified. CALHM1 was found to encode an integral membrane glycoprotein containing several key characteristics of a $Ca^{2+}$ release channel. CALHM1 controls cytosolic $Ca^{2+}$ levels, homomultimerizes, and shares strong sequence similarities with the predicted selectivity filter of NMDAR (FIGS. 3 and 4). Importantly, it was also demonstrated that CALHM1 contains a functionally important N residue at position 72 that aligns with the Q/R/N site of the NMDAR selectivity filter (FIG. 4). Thus, NMDAR and CALHM1 share important structural similarities at the sequence level in a region that was previously described to be a critical determinant for $Ca^{2+}$ selectivity and permeation by glutamate receptor ion channels (Wollmuth and Sobolevsky, 2004). Furthermore, it was shown that CALHM1 localizes to the cell surface where its C-terminal end is extracellularly oriented, suggesting that CALHM1 function may be regulated by extracellular ligands.

Figure 5:
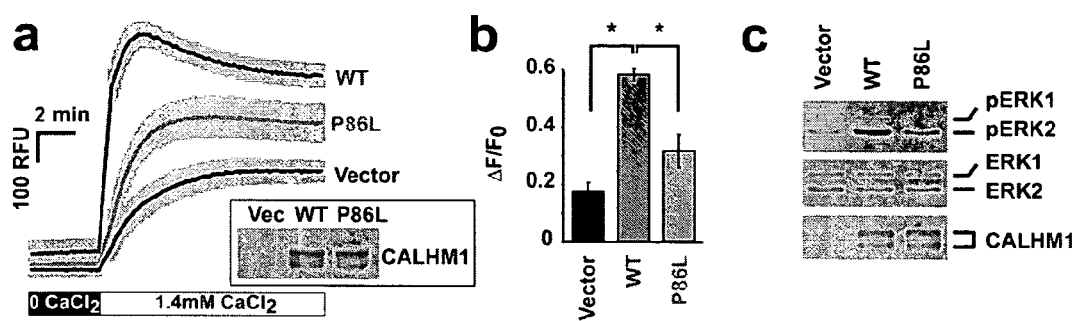
FIG. 5 is graphs and photographs of WBs showing the CALHM1 P86L polymorphism impairs $[Ca^{2+}]_i$ and ERK1/2 phosphorylation. Panel a shows the cytoplasmic $Ca^{2+}$ measurements in HT-22 cells transfected with control vector and WT or P86L mutated Myc-CALHM1. Cells were treated and results analyzed as in FIG. 3A (n=3 independent experiments). Insert, WB of the corresponding cell lysates with anti-Myc antibody. Panel b shows peak $[Ca^{2+}]_i$ measurements as in Panel a, expressed in $\Delta F/F_0$; *, P<0.001 (Student's t test). Panel c shows western blots of HT-22 cells transfected with vector and WT or P86L mutated Myc-CALHM1 analyzed by "$Ca^{2+}$ add-back" assays and exposed to $CaCl_2$ for 30 min. Cell lysates were probed with antibodies directed against pERK1/2, ERK1/2, and Myc (lowest blot).

In the present report compelling evidence was provided that the rs2986017 SNP in CALHM1, which results in the P86L substitution, is associated with both an increased risk for LOAD and a dysregulation of $Ca^{2+}$ homeostasis (Table 1 and FIG. 5). Specifically, it was shown that the CALHM1 P86L polymorphism leads to reduced levels of cytosolic $Ca^{2+}$ and activated ERK1/2. A large body of literature supports the notion that a deranged intracellular $Ca^{2+}$ signaling is occurring in AD and may be involved in neurodegeneration (Khachaturian, 1989; LaFerla, 2002; Mattson et al., 2000). However, it remains uncertain whether $Ca^{2+}$ signaling interacts with pathways that involve the formation of neurofibrillary tangles (Davies, 2000) and senile plaques (Hardy and Selkoe, 2002), two characteristic cerebral lesions formed by the deposition of hyperphosphorylated tau protein and amyloid-β (Aβ peptide), respectively. The present results provide strong genetic evidence supporting the $Ca^{2+}$ hypothesis of AD (Khachaturian, 1989; LaFerla, 2002; Mattson et al., 2000).

It is well established that highly regulated $Ca^{2+}$ signals in hippocampal neurons control synaptic plasticity and memory formation by activating specific kinases, including ERK1/2 (Rao and Finkbeiner, 2007; Blitzer, 2005; Bardo et al., 2006). Indeed, upon excitatory neurotransmission several glutamate receptors, including NMDAR, are activated to trigger synaptic changes and memory storage by gating $Ca^{2+}$ trough the postsynaptic membrane to promote kinase activation, gene transcription, and protein synthesis (Vao and Finkbeiner, 2007). These results have shown that CALHM1 is predominantly expressed in the brain and therefore suggest that the CALHM1 P86L polymorphism may critically impair neuronal $Ca^{2+}$ homeostasis and the resulting ERK1/2-dependent transcriptional control of neurotransmission, a mechanism that could lead over time to the synaptic degeneration and neuronal loss observed in AD.

The present data further demonstrate the utility of tissue-specific data mining for identifying novel genes potentially involved in LOAD. Beside CALHM1, the screen has identified two additional candidate genes located in linkage regions on chromosomes 2 and 19. Interestingly, these genes are involved in the signaling by TGF-β and IGF receptors, two pathways critical for the control of ERK1/2 activation. This suggests the intriguing possibility that ERK1/2 signaling deregulation could represent a common feature for the disease susceptibility. Beyond AD genetics, however, our bioinformatics methods may have important ramifications in other research areas. Indeed, genome-wide association studies on large population samples represent so far the only reliable approach for identifying modest susceptibility variants for common and complex diseases. It is shown here that comparing tissue-specific gene expression profiles with genetic linkage data may represent a promising alternative screening strategy for identifying candidate genes for other disorders that affect isolated tissues or organs, such as heart disease or cancer.

CALHM1 is a member of a three-gene family whose members differ by their tissue expression profiles. While CALHM1 is mostly expressed in the brain (FIG. 2A), CALHM2 is predicted to be widely expressed. The following expression profiles were predicted with TissueInfo:

Predicted expression profile of CALHM2. Expressed most abundantly in uterus. Expression was also detected in pancreas, dorsal root ganglion, ganglion, muscle, corpus callosum, leukocyte, kidney, liver, gland, pancreatic islets, prostate, fibroblast, colon, mammary gland, amygdala, lung, thalamus, stem cell, artery, spleen, hippocampus, alveolar macrophage, thymus, eye, gut, skin, optic nerve, adrenal gland, heart, hypothalamus, ovary, cartilage, medulla oblongata, brain, placenta, testis, cervix, oligodendrocyte, subthalamus, bone, breast, adipose, epithelium, head, astrocyte, T cell and central ns. Thus, CALHM2 expression was found in heart, an organ where $Ca^{2+}$ homeostasis is critical to normal physiology (Schneeberger et al., 2005).

Predicted expression profile of CALHM3. Expressed most abundantly in placenta. Expression also detected in lymphocyte and cervix.

Methods

TissueInfo tissue expression profiles. Known and predicted transcripts were obtained from Ensembl (human build NCBI35). Ensembl transcripts were filtered for repetitive sequence regions with RepeatBeater (graciously provided by Dr. Coward) (Schneeberger et al., 2005). Similarity searches between human ESTs and human Ensembl transcripts were conducted with megablast (Zhang et al., 2000). ESTs that matched transcripts with less than 95% sequence identity or over less than 150 base pairs were rejected (timegablast parameters—error 0.05-required-length 150-assemblehsps). The resulting matches were processed with tiquery to produce whole genome tissue expression profiles. The programs timegablast and tiquery are from the TissueInfo distribution (Skrabanek and Campagne, 2001; icb.med.cornell.edu/crt/tissueinfo/index.xml). Whole genome profiles were filtered with InsightfulMiner 7.0 (Insightful Corp.) to extract the subset of transcripts annotated by TissueInfo as 'specific to hippocampus'.

LOAD locus screen. The 30 transcripts predicted to be specific to hippocampus by TissueInfo were annotated with their genomic location using EnsMart/Biomart (Kasprzyk et al., 2004) using data from Ensembl. Chromosome numbers and FISH band locations were used to identify those transcripts that matched a locus of susceptibility for Alzheimer's Disease, as documented in AlzGene (Bertram et al. 2007).

Phylogeny prediction. Orthologs of CALHM1 were obtained from complete genomes available from Ensembl build 36 (Kasprzyk et al., 2004). A multiple sequence alignment of human CALHM1, CALHM2, CALHM3 and CALHM1 orthologs was constructed with T-coffe v 4.45 (NOtredame et al., 2002) and manually inspected. Phylogenetic trees constructed with JalView indicated an erroneous mouse ortholog assignment. The most likely CALHM1 mouse ortholog was found to be RefSeq XP_921421. This sequence was used to construct the phylogenetic tree shown in FIG. 1. The phylogenetic tree was created with Phylip (Felsenstein, 2005) and the tree rendered as an unrooted tree with Phylodendron (iubio.bio.indiana.edu/treeapp/treeprintform.html).

Materials and antibodies. Tunicamycin, PNGase F, $GdCl_3$, and β-mercaptoethanol were obtained from Sigma. Xestospongin C, 2-APB, dantrolene, PD98059, and BAPTA-AM were from Calbiochem. Forskolin was from MP Biomedicals. Anti-Myc antibody (clone 9E10) was from Chemicon and anti-calreticulin antibody from ABR Affinity BioReagents. Anti-actin antibody was from BD Transduction Laboratories. Anti-ERK1/2 and anti-phospho-ERK1/2 antibodies were from Cell Signaling Technology.

RT-PCR. Total human RNA preparations (1 µg, Clontech) from several brain regions (total brain, hippocampus, cerebellum, cerebral cortex, temporal lobe, frontal lobe, occipital pole) and 20 human tissues (Human Total RNA Master Panel II) were subjected to RT reactions using M-MLV-RT and random hexamer primers (Invitrogen). Ten percent of the RT reactions was used for the following PCR assays using GoTaq Flexi DNA polymerase (Promega). β-Actin PCR was performed with 0.4 µM primer (BAC1004: CTC CTT AAT GTC ACG CAC GAT TTC [SEQ ID NO:1] and BAC1008: GCC AAC CGC GAG AAG ATG ACC [SEQ ID NO:2]; Maxim Biotech) and 1.5 mM $MgCl$, under the following cycle conditions: 3 min denaturation at 94° C. and 30 cycles with 30 seconds at 94° C., 30 seconds at 58° C., 45 seconds at 72° C. Amplification of human CALHM1 was done with 0.4 µM primer F370 (5'-TGC TTC CTC TGT GCC TTC TG-3'-SEQ ID NO:3) and F777 (5'-CTC CAG GTC ATG GTT CAT GG-3'-SEQ ID NO:4) and 1.25 mM $MgCl_2$ under the following conditions: Denaturation for 3 min at 94° C. and 35 cycles with 30 seconds at 94° C., annealing for 30 seconds at 58° C., and extension for 30 seconds at 72° C. with a subsequent final extension at 72° C. for 10 min. PCR reactions were run in an Eppendorf Master gradient cycler.

CALHM1 subcloning and mutagenesis. Human CALHM1 cDNA (formerly annotated as FAM26C) was obtained from ATCC. The translated part of the cDNA was subcloned in frame with the carboxy-terminated Myc-His tag into pcDNA3.1 vector for overexpression experiments. To investigate protein oligomerization, CALHM1 was subcloned into pcDNA3.1-V5 tag vector. The P86L and N72G mutations were introduced by using the QuikChange II site-directed mutagenesis kit (Stratagene) and confirmed by sequencing of the entire CALHM1 insert.

Cell culture and transfections. All cell lines were tested negative for mycoplasma using MycoSensor PCR Assay Kit (Stratagene). Mouse hippocampal HT-22 cells were kindly provided by Dr. D. Schubert, Salk Institute, La Jolla, Calif. HEK293 cells were from ATCC. Cell lines were maintained in Dulbecco's Modified Earle's Medium (DMEM) supplemented with 10% fetal bovine serum (Hyclone), 2 mM L-glutamine, and penicillin and streptomycin (Invitrogen). All cell lines were transiently transfected with wild type or mutated CALHM1 cDNAs at a cell density of about 50% using Lipofectamine PLUS reagent (Invitrogen) for HEK293 or Lipofectamine 2000 (Invitrogen) for HT-22 cells.

Immunofluoresence analysis. HT-22 cells grown on glass coverslips were transfected as described above. Cells were fixed five hours after transfection with 4% paraformaldehyde in Phosphate Buffered Saline (PBS) for 10 min at 37° C. Cells were then permeabilized or not with 0.1% Triton X-100 for 3 min at room temperature (RT) and blocked with Pierce Superblock in PBS. Cells were incubated at 37° C. with anti-Myc (1:100) and anti-calreticulin (1:2000) primary antibodies for 120 min, and with Alexa Fluor 488 and 594 anti-IgG secondary antibodies (1:2000, Molecular Probes) for 1 h. Cells were then visualized under a Nikon Eclipse TE2000-S fluorescent microscope.

Western blotting (WB) and immunoprecipitation (IP) assays. For WB, cells were washed with PBS and solubilized in ice-cold HEPES buffer (25 mM HEPES, pH 7.4, 150 mM NaCl, 1X Complete protease inhibitor cocktail, Roche) containing 1% SDS. Ten micrograms of extracts was analyzed by SDS-PAGE. A standard ECL detection procedure was then used. For multimerization analyses and IP, cells were harvested six hours after transfection with the indicated CALHM1 cDNAs. Cells were then solubilized for 2 h at 4° C. in HEPES buffer containing 1% Nonidet P-40. Cell extracts were pre-cleared by centrifugation at 10,000 rpm for 5 min. For multimerization analyses, cell extracts were analyzed by WB in the absence (non-reducing conditions) or presence of 5% β-mercaptoethanol (reducing conditions). For IP, supernatants were immunoprecipitated with immobilized anti-Myc antibody, as per supplier's instructions (ProFound Mammalian c-Myc Tag IP Kit, Pierce). Total extracts and immunoprecipitated proteins were then analyzed by WB.

CALHM1 deglycosylation. HEK293 cells were transiently transfected for six hours with CALHM1 cDNA in the absence or presence of 10 µg/ml tunicamycin. CALHM1-transfected HT-22 cells were solubilized and incubated for 16 h at 37° C. in digestion buffer (50 mM $NaH_2PO_4$, pH 7.4, 20 mM EDTA, 0.2% SDS, and 1% β-mercaptoethanol) in the absence or presence of PNGase F. Cell lysates were then analyzed by WB using anti-Myc antibody, as described above.

$Ca^{2+}$ measurements and "$Ca^{2+}$ add-back" assays. Free cytosolic $Ca^{2+}$ was measured in transiently transfected HT-22 cells plated in 6 well plates and loaded with the fluorescent $Ca^{2+}$ indicator Fluo-4. 5.5 h post-transfection, cells were loaded with Fluo-4 as per manufacturer's recommendations (Fluo-4 NW Calcium Assay Kit, Molecular Probes). For "$Ca^{2+}$ add-back" assays, cells were washed with $Ca^{2+}/Mg^{2+}$- free PBS and incubated for 10 min in the absence or presence of the indicated inhibitors in $Ca^{2+}/Mg^{2+}$-free Hanks' balanced salt solution (HBSS), supplemented with 20 mM HEPES buffer, 0.5 mM $MgCl_2$, and 0.4 mM $MgSO_4$. $Ca^{2+}$ was then added back to a final concentration of 1.4 mM. Fluorescence measurements were obtained using a Tecan GENios Pro plate reader at 485 nm excitation and 535 nm emission. Experiments were carried out at RT. Cells were then washed with PBS and analyzed by WB.

CALHM1 sequencing. CALHM1 exons were completely sequenced using genomic DNA preparations obtained from 13 non-AD control individuals and 24 autopsy-confirmed AD patients. Subjects and genomic DNA preparations were described elsewhere (Conrad et al., 2002). Exons and intron/exon boundaries were amplified by PCR using the following primer sequences: FX1US 5'-TCT GGA GGC CAG CAG TGA GT-3' (SEQ ID NO:5)(exon 1), FX1DSa 5'-TTT TGA GAG GTA GGG GGA TAG G-3'(SEQ ID NO:6)(exon 1) and FX2US 5'-GCT TTG GGA GTC TGA ACA GG-3' (SEQ ID NO:7)(exon 2) FX2DS 5'-TCC TTT TTC CAC CTG GTT TG-3' (SEQ ID NO:8)(exon 2). PCR conditions were as follows: Initial denaturation for 3 min at 94° C. and 35 cycles of 30 seconds at 94° C., annealing for 30 seconds at 54° C. (exon 1) or 53° C. (exon 2) and extension for 1 min at 72° C. for 35 cycles. ExoSAP purified PCR products were sequenced by GeneWiz.

SNP analyses—Population. The French AD and control subjects were all Caucasian (AD cases n=710, age at study=72.1±7.7 years, age at onset=68.7±8.1 years, 38.7% male; Controls n=565, age=72.1±8.0 years, 39.4% male). A diagnosis of probable AD was established according to DSM-III-R and NINCDS-ADRDA criteria. Caucasian controls were defined as subjects without DMS-III-R dementia criteria, with integrity of cognitive function and with a MMS score≧25. Controls were recruited from retirement homes or from electoral rolls (altruistic volunteers). Each individual or next of kin gave informed consent. Control subjects with a family history of dementia were excluded.

Genotyping. The P86L genotype was determined by genomic DNA amplification of (i) a 114 bp fragment using the forward mismatched primer 5'-GAAGAGTGGAAGCG-GCCAC-3' (SEQ ID NO:9) and reverse primer 5'-GACGGC-CACCCAGACGACA-3' (SEQ ID NO:10) following by Bsr I digestion and/or (ii) a 141 bp fragment using the forward mismatched primer 5'-GAAGAGTGGAAGCGGCAGC-3' (SEQ ID NO:11) and reverse primer 5'-GAGGAAG-CATTTGCCGTCG-3' (SEQ ID NO:12), followed by Alu I digestion. The genotyping of 176 individuals were checked by direct sequencing of a 207 bp fragment using the forward primer 5'-CCTGGTGCTCTTTCTGCTTG-3' (SEQ ID NO:13) and reverse primer 5'-CAGAAGGCAGAG-GAAGCA-3' (SEQ ID NO:14). Only two discrepancies were observed between CC and CT genotypes.

SNP analyses—Statistical analyses. The SAS software release 8.02 was used (SAS Institute, Cary, N.C.). Univariate analysis was performed using Pearson's $\chi^2$ test. The allele and genotype distributions were considered different between the AD and control populations when $p<0.05$. The association of the P86L polymorphism with the risk of developing AD was assessed by a multiple logistic regression model adjusted for age, gender, and the APOE status. Interactions between age, gender, or APOE and the P86L polymorphism were tested by logistic regression. No significant statistical interactions were detected. Finally, the potential impact of the P86L polymorphism on age at onset was assessed using a general linear model.

Tissue Expression Profiles of CALHM2 and CALHM3. TissueInfo (Skrabanek and Campagne, 2001) was used to predict the expression of CALHM2 and CALHM3 in human tissues. The predicted expression profiles are respectively: CALHM2: Expressed most abundantly in uterus. Expression also detected in "pancreas, dorsal root ganglion, ganglion, muscle, corpus callosum, leukocyte, kidney, liver, gland, pancreatic islets, prostate, fibroblast, colon, mammary gland, amygdala, lung, thalamus, stem cell, artery, spleen, hippocampus, alveolar macrophage, thymus, eye, gut, skin, optic nerve, adrenal gland, heart, hypothalamus, ovary, cartilage, medulla oblongata, brain, placenta, testis, cervix, oligodendrocyte, subthalamus, bone, breast, adipose, epithelium, head, astrocyte, t cell, central ns". CALHM3: Expressed most abundantly in placenta. Expression also detected in "lymphocyte, cervix".

Notes. CALHM1 (also called FAM26C) has Ensembl accession code ENSG00000185933 (Uniprot Q8IU99). CALHM3 (FAM26A; Ensembl ENSG00000183128; Uniprot Q86XJ0). CALHM2 (FAM26B; Ensembl ENSG00000138172; Uniprot Q9HA72). Genes with significant sequence similarity to CALHM1 in human include FAM26D (Uniprot Q5JW98), FAM26E (Uniprot Q8N5C1), and FAM26F (Uniprot Q5R3K3). Ensembl accession codes refer to Ensembl release 43.

Example 2

CALHM1 and Aβ Accumulation

In order to gain insight into the relevance of the rs2986017 SNP for the disease, the effect of the corresponding P86L substitution on $Ca^{2+}$ homeostasis was investigated. Importantly, it was observed that the P86L mutation caused a significant inhibition of the effect of CALHM1 on $[Ca^{2+}]_i$ (FIGS. 5a and 5b). Cytosolic $Ca^{2+}$ is a remarkably versatile signal that controls multiple pathways including APP metabolism (LaFerla, 2002). It was therefore asked whether CALHM1 P86L polymorphism affects Aβ levels in APP-transfected cells. While it was found that overexpression of wild type CALHM1 resulted in a robust decrease in the accumulation of both Aβ1-40 and Aβ1-42 under $Ca^{2+}$ add-back conditions, P86L-mutated CALHM1 was unable to noticeably influence Aβ levels. These results demonstrate that CALHM1, by increasing cytosolic $Ca^{2+}$, is able to repress Aβ accumulation. Strikingly, P86L polymorphism was found to lead to an inhibition of CALHM1 function resulting in a significant elevation of Aβ levels.

```
SEQ ID NOs
DNA-artificial-β-actin PCR primer
                                                        SEQ ID NO: 1
CTC CTT AAT GTC ACG CAC GAT TTC DNA-artificial-β-actin PCR primer
                                                        SEQ ID NO: 2
GCC AAC CGC GAG AAG ATG ACC
```

```
DNA-artificial-CALHM1 PCR primer
                                                          SEQ ID NO: 3
TGC TTC CTC TGT GCC TTC TG DNA-artificial-CALHM1 PCR primer
                                                          SEQ ID NO: 4
CTC CAG GTC ATG GTT CAT GG DNA-artificial-CALHM1 exon 1 PCR primer FX1US
                                                          SEQ ID NO: 5
TCT TGG AGG CAG CAG TGA GT DNA-artificial-CALHM1 exon 1 PCR primer FX1DSa
                                                          SEQ ID NO: 6
TTT TGA GAG GTA GGG GGA TAG G DNA-artificial-CALHM1 exon 2 PCR primer FX2US
                                                          SEQ ID NO: 7
GCT TTG GGA GTC TGA ACA GG DNA-artificial-CALHM1 exon 2 PCR primer FX2DS
                                                          SEQ ID NO: 8
TCC TTT TCA CCT GGT TTG DNA-artificial-PCR primer for P86L genotyping
                                                          SEQ ID NO: 9
GAAGAGTGGAAGCGGCCAC DNA-artificial-PCR primer for P86L genotyping
                                                          SEQ ID NO: 10
GACGGCCACCCAGACGACA DNA-artificial-PCR primer for P86L genotyping
                                                          SEQ ID NO: 11
GAAGAGTGGAAGCGGCAGC DNA-artificial-PCR primer for P86L genotyping
                                                          SEQ ID NO: 12
GAGGAAGCATTTGCCGTCG DNA-artificial-PCR primer for P86L genotyping
                                                          SEQ ID NO: 13
CCTGGTGCTCTTTCTGCTTG DNA-artificial-PCR primer for P86L genotyping
                                                          SEQ ID NO: 14
CAGAAGGCAGAGGAAGCA Protein-Human CALHM3/FAM26A
                                                          SEQ ID NO: 15
  1 mdkfrmlfqh fqsssesvmn gicllllaavt vklyssfdfn cpclvhynal yglglllltpp
 61 lalflcglla nrqsvvmvee wrrpaghrrk dpgiirymcs svlqralaap lvwillalld
121 gkcfvcafss svdpekfldf anmtpsqvql flakvpcked elvrdspark aysrylrcls
181 qaigwsvtll liiaaflarc lrpcfdqtvf lqrrywsnyv dleqklfdet ccehardfah
241 rcvlhffasm rselqarglr rgnagrrlel pavpeppavp eppegldsgs gkahlraiss
301 reqvdrllst wysskppldl aaspglcggg lshraptlal gtrlsqhtdv Protein-Human CALHM2/FAM26B
                                                          SEQ ID NO: 16
  1 maaliaenfr flslffkskd vmifnglval gtvgsqelfs vvafhcpcsp arnylyglaa
 61 igvpalvlfi igiilnnhtw nlvaecqhrr tkncsaaptf lllssilgra avapvtwsvi
121 sllrgeayvc alsefvdpss ltareehfps ahateilarf pckenpdnls dfreevsrrl
181 ryesqlfgwl ligvvailvf ltkclkhycs plsyrqeayw aqyranedql fqrtaevhsr
241 vlaannvrrf fgfvalnkdd eelianfpve gtqprpqwna itgvylyren qglplysrlh
301 kwaqglagng aapdnvemal lps Protein-Human CALHM1/FAM26C
                                                          SEQ ID NO: 17
  1 mmdkfrmifq flqsnqesfm ngicgimala saqmysafdf ncpclpgyna aysagillap
 61 plvlfllglv mnnnvsmlae ewkrplgrra kdpavlrymf csmaqralia pvvwvavtll
121 dgkcflcafc tavpvsalgn gslapglpap elarlllarvp cpeiydgdwl larevavryl
181 rcisqalgws fvllttllaf vvrsvrpcft qaaflkskyw shyidierkl fdetctehak
241 afakvciqqf feamnhdlel ghthgtlata pasaaapttp dgaeeerekl rgitdqgtmn
301 rlltswhkck pplrlgqeep plmgngwagg gprpprkeva tyfskv Protein-Mouse CALHM1/FAM26C
                                                          SEQ ID NO: 18
  1 mdkfrmifqf lqsnqesfmn gicgimalas aqmysafdfn cpclpgynvv yslgillltpp
 61 lvlfllglvm nnnismlaee wkrpagrrak dpavlrymfc smaqraliap vvwvavtlld
121 gkcflcafct avpvatlgng slvpglpape larllarvpc peiydgnwll arevavrylr
181 cisqalgwsf vllttllafv vrsvrpcftq vaflkskyws hyidierklf detctehaka
```

-continued

```
241 fakvciqqff eamnhdlelg hthgvlatat atatateavq spsdrteeer eklrgitdqg
301 tmnrlltswh kckpplrlgq eaplmsngwa ggeprpprke vatyfskv
```

Protein-*C. elegans* CALHM1/FAM26C-GenBank NP_495403

SEQ ID NO: 19

```
  1 mttsinsvvt vfqnvftnhg stllngilia ttvgqqslvr kltfscpcay piniyhslvf
 61 mfgptaalll igitvnsttw klahgfffrv rdtrhswktt cvswievliq ssvapiawlf
121 vvfldggyyr cyrshefcli sdailcknst ilnsyastss fnkisdngky cppcicvpnp
181 tdasyleaes qiyawglllf sgvaaflvit cnrmcdkytl vqrqyvetyk nvetqkfdav
241 akehasqlae hnaraffgqk dwtkrdwdwv sgipevnnpl farlrliaae ktqqtmytpl
301 qlwndnkgyr ipqpdlqltq iivdetked
```

Protein-Human NMDAR2D (partial sequence)

SEQ ID NO: 20 siwllwalvfnnsvpven

Protein-Human NMDAR2C (partial sequence)

SEQ ID NO: 21 svwllwalvfnnsvpien

Protein-Human NMDAR2B (partial sequence)

SEQ ID NO: 22 aiwllwglvfnnsvpvqn

Protein-Human NMDAR2A (partial sequence)

SEQ ID NO: 23 aiwllwglvfnnsvpvqn

Protein-Human CALHM1 (partial sequence)

SEQ ID NO: 24 lvlfllglvmnnnvsmla

Protein-Chimpanzee CALHM1 (partial sequence)

SEQ ID NO: 25 lvlfllglvmnnnvsmla

Protein-macaque CALHM1 (partial sequence)

SEQ ID NO: 26 lvlfllglvmnnnvsmla

Protein-Opossum CALHM1 (partial sequence)

SEQ ID NO: 27 lvlfllglvmnnnvsmla

Protein-Elephant CALHM1 (partial sequence)

SEQ ID NO: 28 lvlfllglvmnnnvsmla

Protein-Cat CALHM1 (partial sequence)

SEQ ID NO: 29 lvlfllglvmnnnvsmla

Protein-Cow CALHM1 (partial sequence)

SEQ ID NO: 30 lvlfllglvmnnnvsmla

Protein-Rat CALHM1 (partial sequence)

SEQ ID NO: 31 lvlfllglvmnnnismla

Protein-Mouse CALHM1 (partial sequence)

SEQ ID NO: 32 lvlfllglvmnnnismla

Protein-Dog CALHM1 (partial sequence)

SEQ ID NO: 33 lvlfllglvmnnnvsvla

Protein-Platypus CALHM1 (partial sequence)

SEQ ID NO: 34 avlfllglvmnnnvsmla

Protein-Armadillo CALHM1 (partial sequence)

SEQ ID NO: 35 lllfllglvlnnnvsmla

Protein-Hedgehog CALHM1 (partial sequence)

SEQ ID NO: 36 lllfllglvlnnnvsmla

Protein-Chicken CALHM1 (partial sequence)

-continued lilfllgfvlnnnvsmla

Protein-Zebrafish CALHM1 (partial sequence)

SEQ ID NO: 38 iwffllgfvlnnnvsmla

Protein-Medaka CALHM1 (partial sequence)

SEQ ID NO: 39 iwffllgfvlnnnvsvla

Protein-Tetraodon CALHM1 (partial sequence)

SEQ ID NO: 40 iwffmlgfvlnnnvsvla

Protein-Fugo CALHM1 (partial sequence)

SEQ ID NO: 41 iwffmlgfvlnnnvsvla

Protein-Stickleback CALHM1 (partial sequence)

SEQ ID NO: 42 vwffligfvlnnkvsvlt

DNA-Human-SNP rs2986017

SEQ ID NO: 43
ACCTGAGCAG AGGCCCCATT TTGAGAGGTA GGGGGATAGG GCCCTCCCAG AGGGACCTTG
ATCTGCCAGG GAGACCCAGC GTGAAGCCAT GCGGCCCCTC ACCTGGGAGA TGCAGCGGAG
GTAACGCACG GCCACCTCTC GGGCCAACAG CCAGTCGCCA TCGTAGATCT CAGGGCAGGG
CACCCGGGCC AGCAGGCGGG CGAGCTCGGG GGCAGGAAGG CCGGGTGCCA GGCTGCCGTT
GCCCAGTGCG CTCACGGGCA CGGCAGTGCA GAAGGCACAG AGGAAGCATT TGCCGTCGAG
TAGCGTGACG GCCACCCAGA CGACAGGCGC GATGAGGGCG CGCTGGGCCA TGGAGCAGAA
CATGTAGCGC AACACAGCGG GGTCCTTGGC CCGGCGGCCC
(A/G)
GCGGCCGCTT CCACTCTTCG GCCAGCATGG ACACGTTGTT GTTCATGACC AGGCCAAGCA
GAAAGAGCAC CAGGGGTGGC GCCAGCAGGA TGCCCGCGCT GTAGGCTGCA TTGTAGCCCG
GCAGGCAGGG GCAGTTGAAG TCGAAGGCCG AGTACATCTG GGCACTGCC AGGGCCATGA
TGCCACAGAT GCCATTCATG AAGGACTCCT GGTTGGACTG CAGGAACTGG AAGATCATCC
GGAACTTGTC CATCATGCCC GCTGTGGGGC CCGGCCTCCT CTTCCCAACT CACTGCTGCC
TCCAAGAGGG CCCCTGCTGC CCACCCTGCC CACTGGGTGC CCACCTCATG ACTCGGGCTC
TCCTGGCTGG GACCAACAGA GCTCAGAGCA GAGGCTGAGG

REFERENCES

F. M. Ashcroft, *Nature* 440, 440-7 (Mar. 23, 2006).
D. J. Balding, *Nature Reviews|Genetics* 7, 781-91 (2006).
S. Bardo, M. G. Cavazzini, N. Emptage, *Trends Pharmacol Sci* 27, 78-84 (February 2006).
M. J. Berridge, M. D. Bootman, H. L. Roderick, *Nat Rev Mol Cell Biol* 4, 517-29 (July 2003).
L. Bertram, D. Blacker, K. Mullin, D. Keeney, J. Jones, S. Basu, S. Yhu, M. G. McInnis, R. C. Go, K. Vekrellis, D. J. Selkoe, A. J. Saunders. R. E. Tanzi, *Science* 290, 2302-3 (Dec. 22, 2000).
L. Bertram, M. B. McQueen, K. Mullin, D. Blacker, R. E. Tanzi, *Nat Genet* 39, 17-23 (January 2007)
D. Blacker, L. Bertram, A. J. Saunders, T. J. Moscarillo, M. S. Albert, H. Wiener, R. T. Perry, J. S. Collins, L. E. Harrell, R. C. Go, A. Mahoney, T. Beaty, M. D. Fallin, D. Avramopoulos, G. A. Chase, M. F. Folstein, M. G. McInnis, S. S. Bassett, K. J. Doheny, E. W. Pugh, R. E. Tanzi, *Hum Mol Genet* 12, 23-32 (Jan. 1, 2003).
R. D. Blitzer, *Sci STKE* 2005, tr26 (Nov. 8, 2005).
H. Braak, E. Braak, *Acta Neuropathol (Berl)* 82, 239-59 (1991).
F. Campagne, L. Skrabanek, *BMC Bioinformatics* 7, 481 (2006).
C. Conrad, C. Vianna, M. Freeman, P. Davies, *Proc Natl Acad Sci USA* 99, 7751-6 (May 28, 2002).
P. Davies, *Ann NY Acad Sci* 924, 8-16 (2000).
M. J. de Leon, S. DeSanti, R. Zinkowski, P. D. Mehta, D. Pratico, S. Segal, C. Clark, D. Kerkman, J. DeBernardis, J. Li, L. Lair, B. Reisberg, W. Tsui, H. Rusinek, *J Intern Med* 256, 205-23 (September 2004).
B. Dermaut, S. Kumar-Singh, R. Rademakers, J. Theuns, M. Cruts, C. Van Broeckhoven, *Trends Genet* 21, 664-72 (December 2005).
R. Dingledine, K. Borges, D. Bowie, S. F. Traynelis, *Pharmacol Rev* 51, 7-61 (March 1999).
D. A. Doyle, J. Morals Cabral, R. A. Pfuetzner, A. Kuo, J. M. Gulbis, S. L. Cohen, B. T. Chait, R. MacKinnon, *Science* 280, 69-77 (Apr. 3, 1998).
N. Ertekin-Taner, N. Graff-Radford, L. H. Younkin, C. Eckman, M. Baker, J. Adamson, J. Ronald, J. Blangero, M. Hutton, S. G. Younkin, *Science* 290, 2303-4 (Dec. 22, 2000).
J. Felsenstein, *Philosophical Transactions of the Royal Society of London. series B* 360, 1427-1434 (2005).
L. A. Farrer, A. Bowirrat, R. P. Friedland, K. Waraska, A. D. Korczyn, C. T. Baldwin, *Hum Mol Genet* 12, 415-22 (Feb. 15, 2003).
M. Gatz, C. A. Reynolds, L. Fratiglioni, B. Johansson, J. A. Mortimer, S. Berg, A. Fiske, N. L. Pedersen, *Arch Gen Psychiatry* 63, 168-74 (February 2006).
E. Gouaux, R. Mackinnon, *Science* 310, 1461-5 (Dec. 2, 2005).
R. Gupta, E. Jung, B. S., *Manuscript in preparation*.
J. Hardy, D. J. Selkoe, *Science* 297, 353-6 (Jul. 19, 2002).
A. Kasprzyk, D. Keefe, D. Smedley, D. London, W. Spooner, C. Melsopp, M. Hammond, P. Rocca-Serra, T. Cox, E. Birney, *Genome Res* 14, 160-9 (January 2004).
P. Kehoe, F. Wavrant-De Vrieze, R. Crook, W. S. Wu, P. Holmans, I. Fenton, G. Spurlock, N. Norton, H. Williams, N. Williams, S. Lovestone, J. Perez-Tur, M. Hutton, M. C. Chartier-Harlin, S. Shears, K. Roehl, J. Booth, W. Van Voorst, D. Ramic, J. Williams, A. Goate, J. Hardy, M. J. Owen, *Hum Mol Genet* 8, 237-45 (February 1999).

J. L. Kennedy, L. A. Farrer, N. C. Andreasen, R. Mayeux, P. St George-Hyslop, *Science* 302, 822-6 (Oct. 31, 2003).

Z. S. Khachaturian, *Ann NY Acad Sci* 568, 1-4 (1989).

F. M. LaFerla, *Nat Rev Neurosci* 3, 862-72 (November 2002).

V. M. Lee, J. Q. Trojanowski, *Neuron* 52, 33-8 (Oct. 5, 2006).

R. S. Lewis, *Nature* 446, 284-7 (Mar. 15, 2007).

M. Makhinson, J. K. Chotiner, J. B. Watson, T. J. O'Dell, *J Neurosci* 19, 2500-10 (Apr. 1, 1999)

P. Marambaud, N. K. Robakis, *Genes Brain Behav* 4, 134-46 (April 2005).

M. P. Mattson, *Nature* 430, 631-9 (Aug. 5, 2004).

M. P. Mattson, F. M. LaFerla, S. L. Chan, M. A. Leissring, P. N. Shepel, J. D. Geiger, *Trends Neurosci* 23, 222-9 (May, 2000).

A. Myers, P. Holmans, H. Marshall, J. Kwon, D. Meyer, D. Ramic, S. Shears, J. Booth, F. W. DeVrieze, R. Crook, M. Hamshere, R. Abraham, N. Tunstall, F. Rice, S. Carty, S. Lillystone, P. Kehoe, V. Rudrasingham, L. Jones, S. Lovestone, J. Perez-Tur, J. Williams, M. J. Owen, J. Hardy, A. M. Goate, *Science* 290, 2304-5 (Dec. 22, 2000).

C. Notredame, D. G. Higgins. J. Heringa, *J Mol Biol* 302, 205-17 (Sep. 8, 2000).

P. Pastor, A. M. Goate, *Curr Psychiatry Rep* 6, 125-33 (April 2004).

V. R. Rao, S. Finkbeiner, *Trends Neurosci* (Apr. 5, 2007).

K. Schneeberger, K. Malde, E. Coward, I. Jonassen, *Nucleic Acids Res* 33, 2176-80 (2005).

D. J. Selkoe, *Physiol Rev* 81, 741-66. (2001).

L. Skrabanek, F. Campagne, *Nucleic Acids Res* 29, E102-2 (Nov. 1, 2001).

E. L. Sonnhammer, G. von Heijne, A. Krogh, *Proc Int Conf Intell Syst Mol Biol* 6, 175-82 (1998).

W. J. Strittmatter, A. M. Saunders, D. Schmechel, M. Pericak-Vance, J. Enghild, G. S. Salvesen, A. D. Roses, *Proc Natl Acad Sci USA* 90, 1977-81 (Mar. 1, 1993).

G. M. Thomas, R. L. Huganir, *Nat Rev Neurosci* 5, 173-83 (March 2004).

L. P. Wollmuth, A. I. Sobolevsky, *Trends Neurosci* 27, 321-8 (June 2004).

Z. Zhang, S. Schwartz, L. Wagner, W. Miller, *J Comput Biol* 7, 203-14 (February-April 2000).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of screening a test compound for the ability to alter calcium homeostasis in a mammalian cell expressing a CALHM protein, the method comprising experimentally determining whether the test compound affects expression or activity of the CALHM protein, wherein a test compound that affects expression or activity of the CALHM protein has the ability to alter calcium homeostasis in the mammalian cell, wherein the CALHM protein is (i) a CALHM1 protein having an amino acid sequence at least 90% identical to SEQ ID NO: 17, (ii) a CALHM2 protein having an amino acid sequence at least 90% identical to SEQ ID NO: 16, or (iii) a CALHM3 protein having an amino acid sequence at least 90% identical to SEQ ID NO: 15.

2. The method of claim 1, wherein the CALHM I protein has an amino acid sequence at least 99% identical to SEQ ID NO: 17.

3. The method of claim 1, wherein the CALHM I protein has an amino acid sequence completely identical to SEQ ID NO: 17.

4. The method of claim 1, wherein the CALHM I protein has an amino acid sequence completely identical to SEQ ID NO: 17 except for an L86P substitution.

5. The method of claim 1, wherein the test compound is an organic molecule less than 1000 mw.

6. The method of claim 1, wherein the test compound is a polypeptide.

7. The method of claim 6, wherein the polypeptide comprises an antibody binding site.

8. The method of claim 1, wherein the test compound is a nucleic acid.

9. The method of claim 8, wherein the nucleic acid is complementary to a portion of the gene encoding the CALHM 1 protein.

10. A method of screening a test compound for the ability to inhibit ERK 1/2 phosphorylation in a mammalian cell, the method comprising experimentally determining whether the test compound affects expression or activity of a CALHM1 protein having an amino acid sequence at least 90% identical to SEQ ID NO: 17, wherein a test compound that affects expression or activity of the CALHM1 protein has the ability to inhibit ERK 1/2 phosphorylation in the mammalian cell.

11. The method of claim 10, wherein the CALHM I protein has an amino acid sequence at least 99% identical to SEQ ID NO: 17.

12. The method of claim 10, wherein the CALHM 1 protein has an amino acid sequence completely identical to SEQ ID NO: 17.

13. The method of claim 10, wherein the CALHM I protein has an amino acid sequence completely identical to SEQ ID NO: 17 except for an L86P substitution.

14. The method of claim 10, wherein the test compound is an organic molecule less than 1000 mw.

15. The method of claim 10, wherein the test compound is a polypeptide.

16. The method of claim 15, wherein the polypeptide comprises an antibody binding site.

17. The method of claim 10, wherein the test compound is a nucleic acid.

18. The method of claim 17, wherein the nucleic acid is complementary to a portion of the gene encoding the CALHM 1 protein.

19. A method of screening a test compound for the ability to inhibit amyloid-beta peptide accumulation in a mammalian cell or biological fluid, the method comprising experimentally determining whether the test compound affects expression or activity of a CALHM1 protein having an amino acid sequence at least 90% identical to SEQ ID NO: 17, wherein a test compound that affects expression or activity of the CALHM1 protein may have the ability to inhibit amyloid-beta peptide accumulation in the mammalian cell.

20. The method of claim 19, wherein the CALHM 1 protein has an amino acid sequence at least 99% identical to SEQ ID NO: 17.

21. The method of claim 19, wherein the CALHM I protein has an amino acid sequence completely identical to SEQ ID NO: 17.

22. The method of claim 19, wherein the CALHM 1 protein has an amino acid sequence completely identical to SEQ ID NO: 17 except for an L86P substitution.

23. The method of claim 19, wherein the test compound is an organic molecule less than 1000 mw.

24. The method of claim 19, wherein the test compound is a polypeptide.

25. The method of claim 24, wherein the polypeptide comprises an antibody binding site.

26. The method of claim 19, wherein the test compound is a nucleic acid.

27. The method of claim 26, wherein the nucleic acid is complementary to a portion of the gene encoding the CALHM 1 protein.

28. A method of screening for a test compound that may affect Alzheimer's disease, the method comprising experimentally determining whether the compound affects expression or activity of a CALHM1 protein having an amino acid sequence at least 90% identical to SEQ ID NO: 17, wherein a test compound that affects expression or activity of the CALHM1 protein may affect Alzheimer's disease.

29. The method of claim 28, wherein the CALHM I protein has an amino acid sequence at least 99% identical to SEQ ID NO: 17.

30. The method of claim 28, wherein the CALHM I protein has an amino acid sequence completely identical to SEQ ID NO: 17.

31. The method of claim 28, wherein the CALHM I protein has an amino acid sequence completely identical to SEQ ID NO: 17 except for an L86P substitution.

32. The method of claim 28, wherein the test compound is an organic molecule less than 1000 mw.

33. The method of claim 28, wherein the test compound is a polypeptide.

34. The method of claim 33, wherein the polypeptide comprises an antibody binding site.

35. The method of claim 28, wherein the test compound is a nucleic acid.

36. The method of claim 35, wherein the nucleic acid is complementary to a portion of the gene encoding the CALHM I protein.

* * * * *